US008758256B2

(12) United States Patent
O'Laughlin et al.

(10) Patent No.: US 8,758,256 B2
(45) Date of Patent: Jun. 24, 2014

(54) APPARATUS FOR BRACHYTHERAPY THAT USES A SCANNING PROBE FOR TREATMENT OF MALIGNANT TISSUE

(75) Inventors: Michael O'Laughlin, St. Louis, MO (US); Michael Belgeri, Ellisville, MO (US)

(73) Assignee: Best Medical International, Inc., Springfield, VA (US)

(*) Notice: Subject to any disclaimer, the term of this patent is extended or adjusted under 35 U.S.C. 154(b) by 503 days.

(21) Appl. No.: 12/834,384

(22) Filed: Jul. 12, 2010

(65) Prior Publication Data

US 2012/0010512 A1      Jan. 12, 2012

(51) Int. Cl.
*A61B 8/14*          (2006.01)

(52) U.S. Cl.
USPC ........... 600/464; 600/459; 600/461; 600/462; 600/463

(58) Field of Classification Search
None
See application file for complete search history.

(56) References Cited

U.S. PATENT DOCUMENTS

| | | | |
|---|---|---|---|
| 3,946,613 A * | 3/1976 | Silver | 374/183 |
| 4,166,389 A * | 9/1979 | Montren | 374/158 |
| 4,374,525 A | 2/1983 | Baba | |
| 4,756,313 A | 7/1988 | Terwilliger | |
| 4,757,818 A | 7/1988 | Angelsen | |
| 4,771,774 A * | 9/1988 | Simpson et al. | 606/171 |
| 4,802,458 A | 2/1989 | Finsterwald et al. | |
| 4,819,650 A | 4/1989 | Goldstein | |
| 4,841,979 A | 6/1989 | Dow et al. | |
| 4,917,096 A | 4/1990 | Englehart | |
| 4,944,308 A | 7/1990 | Akerfeldt | |
| 5,048,529 A | 9/1991 | Blumenthal | |
| 5,050,610 A | 9/1991 | Oaks et al. | |
| 5,054,491 A | 10/1991 | Saito et al. | |
| 5,070,879 A | 12/1991 | Herres | |
| 5,090,414 A | 2/1992 | Takano | |
| 5,105,819 A | 4/1992 | Wollschlager et al. | |

(Continued)

FOREIGN PATENT DOCUMENTS

| | | |
|---|---|---|
| EP | 0142862 | 5/1985 |
| EP | 0453014 | 10/1991 |

(Continued)

OTHER PUBLICATIONS

"Execution of Robot-Assisted Biopsies Within the Clinical Context," Rovetta et al, Journal of Image Guided Surgery, 1: 280-287, 1995.

(Continued)

*Primary Examiner* — Long V. Le
*Assistant Examiner* — Bradley Impink

(57) ABSTRACT

The invention includes a probe for imaging tissue within a body cavity. The probe includes a housing which has a first substantially narrow elongate distal portion insertable into a body cavity, and a second elongate portion proximal of the first elongate portion. The narrow distal portion houses a transducer which is longitudinally translatable and rotatable relative thereto. The second elongate portion houses a platform assembly and a movable member. The platform assembly includes a transmission system and a frame, both of which are coupled to the transducer by at least one connector such that rotational movement of the platform assembly within the second elongate portion effectuates rotation of the transducer within the first elongate portion, and translational movement of the moveable member within the second elongate portion effectuates translational movement of the transducer within the first elongate portion. The probe is used with a needle assembly and delivery system.

22 Claims, 15 Drawing Sheets

(56) References Cited

U.S. PATENT DOCUMENTS

| | | | |
|---|---|---|---|
| 5,107,844 A * | 4/1992 | Kami et al. | 600/463 |
| 5,152,294 A | 10/1992 | Mochizuki et al. | |
| 5,159,931 A | 11/1992 | Pini | |
| 5,170,793 A * | 12/1992 | Takano et al. | 600/445 |
| 5,181,514 A | 1/1993 | Solomon et al. | |
| 5,331,962 A | 7/1994 | Coleman et al. | |
| 5,361,768 A | 11/1994 | Webler et al. | |
| 5,368,045 A | 11/1994 | Clement et al. | |
| 5,383,460 A * | 1/1995 | Jang et al. | 600/439 |
| 5,394,878 A | 3/1995 | Frazin et al. | |
| 5,398,690 A | 3/1995 | Batten et al. | |
| 5,429,136 A * | 7/1995 | Milo et al. | 600/439 |
| 5,456,258 A | 10/1995 | Kondo et al. | |
| 5,460,179 A | 10/1995 | Okunuki et al. | |
| 5,474,072 A | 12/1995 | Shmulewitz | |
| 5,497,776 A | 3/1996 | Yamazaki | |
| 5,526,822 A * | 6/1996 | Burbank et al. | 600/567 |
| 5,592,942 A | 1/1997 | Webler et al. | |
| 5,611,343 A | 3/1997 | Wilson | |
| 5,634,466 A | 6/1997 | Gruner | |
| 5,660,185 A | 8/1997 | Shulewitz et al. | |
| 5,671,748 A | 9/1997 | Itoi | |
| 5,762,066 A | 6/1998 | Law et al. | |
| 5,769,079 A | 6/1998 | Hossack | |
| 5,810,007 A | 9/1998 | Holupka | |
| 5,842,473 A | 12/1998 | Fenster et al. | |
| 5,873,828 A | 2/1999 | Fujio | |
| 5,875,778 A | 3/1999 | Vroegop | |
| 5,931,788 A | 8/1999 | Keen et al. | |
| 5,951,489 A | 9/1999 | Bauer | |
| 5,964,707 A | 10/1999 | Fenster et al. | |
| 6,004,271 A | 12/1999 | Moore | |
| 6,036,649 A | 3/2000 | Yuasa | |
| 6,102,867 A | 8/2000 | Dieta et al. | |
| 6,149,598 A | 11/2000 | Tanaka | |
| 6,165,136 A | 12/2000 | Nishtala | |
| 6,171,249 B1 | 1/2001 | Chin | |
| 6,200,269 B1 | 3/2001 | Lin et al. | |
| 6,238,336 B1 | 5/2001 | Ouchi | |
| 6,261,234 B1 | 7/2001 | Lin | |
| 6,261,243 B1 | 7/2001 | Burney | |
| 6,315,724 B1 | 11/2001 | Berman et al. | |
| 6,390,973 B1 | 5/2002 | Ouchi | |
| 6,409,666 B1 | 6/2002 | Ito | |
| 6,425,867 B1 * | 7/2002 | Vaezy et al. | 600/439 |
| 6,447,477 B2 | 9/2002 | Burney et al. | |
| 6,485,411 B1 | 11/2002 | Konstorum et al. | |
| 6,565,588 B1 | 5/2003 | Clement et al. | |
| 6,685,648 B2 | 2/2004 | Flaherty et al. | |
| 6,689,067 B2 | 2/2004 | Sauer et al. | |
| 6,709,397 B2 | 3/2004 | Taylor | |
| 6,712,783 B1 | 3/2004 | Jang | |
| 6,884,219 B1 | 4/2005 | Pruter | |
| 7,066,889 B2 | 6/2006 | Taylor | |
| 7,171,255 B2 | 1/2007 | Holupka et al. | |
| 2002/0002349 A1 | 1/2002 | Flaherty et al. | |
| 2002/0111634 A1 | 8/2002 | Stoianovici et al. | |
| 2003/0073907 A1 * | 4/2003 | Taylor | 600/459 |
| 2003/0078502 A1 | 4/2003 | Miyaki | |
| 2003/0120154 A1 | 6/2003 | Sauer et al. | |
| 2003/0135119 A1 | 7/2003 | Lee et al. | |
| 2003/0158475 A1 * | 8/2003 | Johnson et al. | 600/410 |
| 2004/0030250 A1 | 2/2004 | Stewart | |
| 2004/0133111 A1 | 7/2004 | Szczech | |
| 2004/0204650 A1 | 10/2004 | Taylor | |
| 2005/0119570 A1 | 6/2005 | Lewis et al. | |
| 2005/0159676 A1 | 7/2005 | Taylor et al. | |
| 2005/0203413 A1 | 9/2005 | Fichtinger et al. | |
| 2007/0038126 A1 * | 2/2007 | Pyle et al. | 600/476 |
| 2007/0123797 A1 | 5/2007 | Krause | |
| 2007/0293787 A1 * | 12/2007 | Taylor et al. | 600/562 |
| 2008/0159606 A1 | 7/2008 | Suri et al. | |
| 2008/0161687 A1 | 7/2008 | Suri et al. | |
| 2008/0269588 A1 | 10/2008 | Csavoy et al. | |
| 2009/0048515 A1 | 2/2009 | Suri et al. | |
| 2009/0270737 A1 * | 10/2009 | Thornton | 600/466 |
| 2009/0318832 A1 | 12/2009 | Andreyko et al. | |
| 2010/0036293 A1 | 2/2010 | Isola et al. | |
| 2011/0201976 A1 * | 8/2011 | Sanghvi et al. | 601/2 |

FOREIGN PATENT DOCUMENTS

| | | |
|---|---|---|
| EP | 0504480 | 9/1992 |
| WO | WO9316641 | 9/1993 |
| WO | WO0108561 | 2/2001 |
| WO | WO03088833 | 10/2003 |

OTHER PUBLICATIONS

"Transrectal Prostate Biopsy Inside Closed MRI Scanner with Remote Actuation, under Real-Time Image Guidance," Fichtinger et al, MICCAAI 2002, LNCS 2488 pp. 91-98, 2002.

"A Robotic System for Transrectal Needle Insertion into the Prostate with Integrated Ultrasound", Chad M. Schneider et al., Proceedings of the 2004 IEEE Interntational conference on Robotics & Automation, Apr. 2004, pp. 365-370.

Parker Aquasonic Clear Ultrasound Transmission Gel 8 oz *(.25L) for Ultrasonic Conductivity, EZUltrasound.com, downloaded on Apr. 27, 2010, available at http://ezultrasound.com/aquasonic8oz.aspx.

Three-Dimensional Rigid and Non-Rigid Image Registration for the Pelvis and Prostate, Baowei Fei et al, Handbook of Medical Image Analysis, 2005,, Chapter 3, pp. 103-149.

Closed-Loop Control in Fused MR-TRUS Image-Guided Prostate Biopsy, Sheng Xu et al, NIH Public Access Author Manuscript, 2008.

Registering Histological and MR Images of Prostate for Imagebased Cancer Detection, Yiqiang Zhang et al, NIH Public Access Manuscript, 26 pages, 2008.

Ergonomic Biopsy Gun, Ofer Gofrit MD,PhD, Hadasit, downloaded Apr. 28, 2010, available at www.hadasit.co.il/category/ergonomic-biopsy-gun.

Prostate Ultrasound and Biopsy, Monterey Bay Urology Association, downloaded Apr. 28, 2010, available at www.montereybayurology.com/officepro/ProstateUltrasoundandBiopsy.htm.

Stereotactic Biopsy Operation Types, GE Healthcare Product Specifications, downloaded Apr. 27, 2010, available at www.gehealthcare.com/usen/xr/mammo/products/sbiopsy_optype.html.

U.S. Appl. No. 60/493,406, Fichtinger et al., Aug. 7, 2003.

* cited by examiner

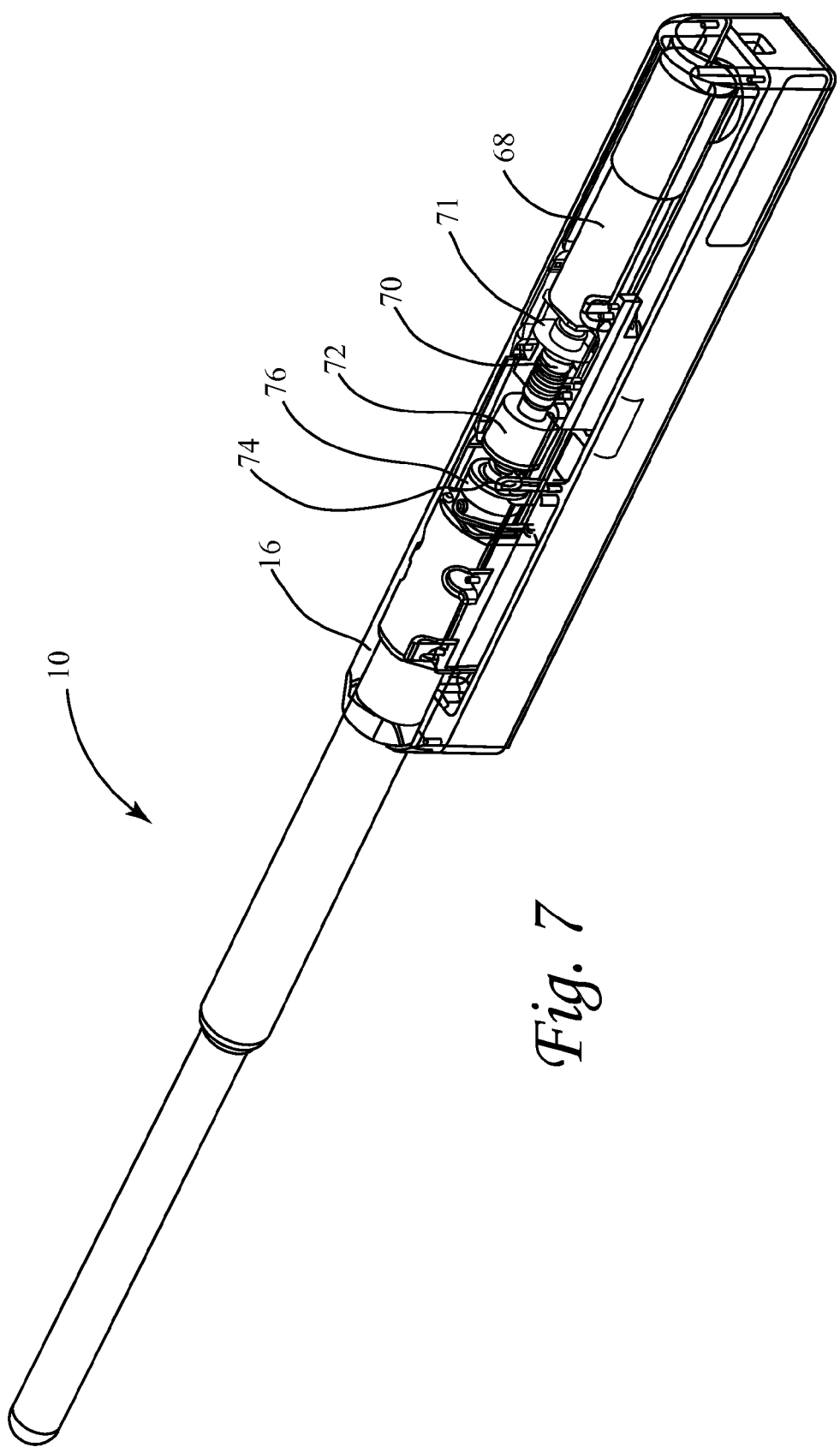

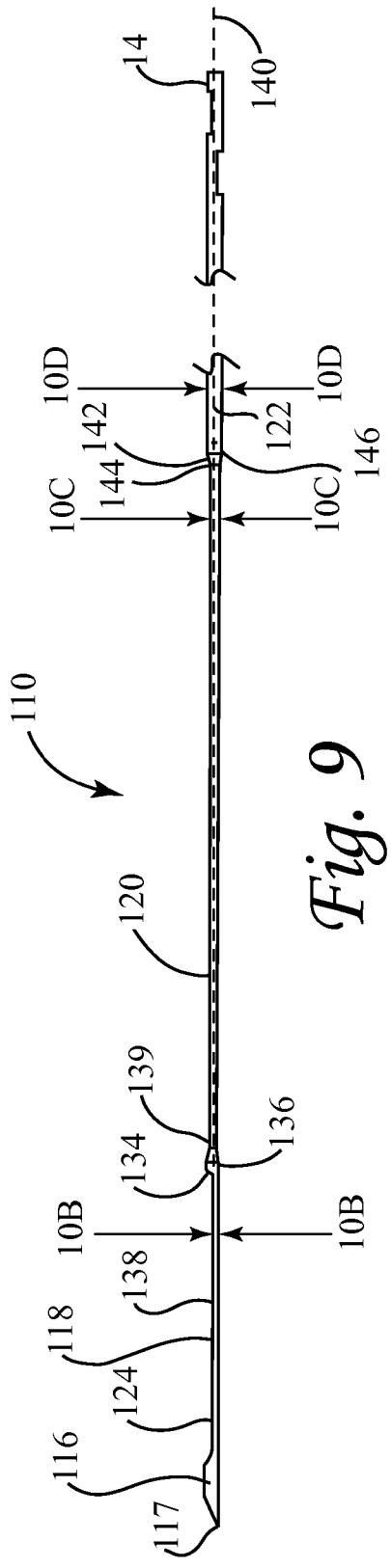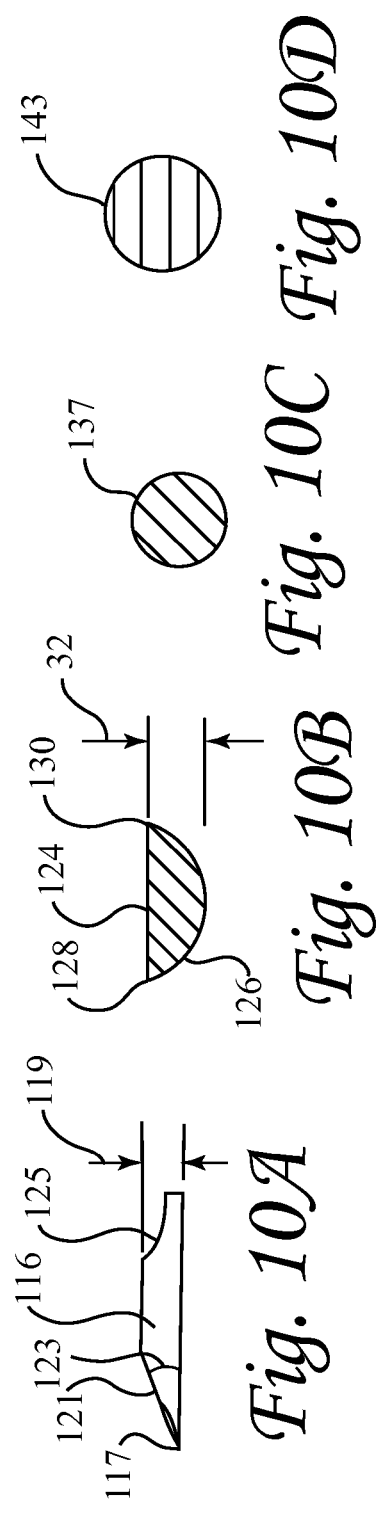

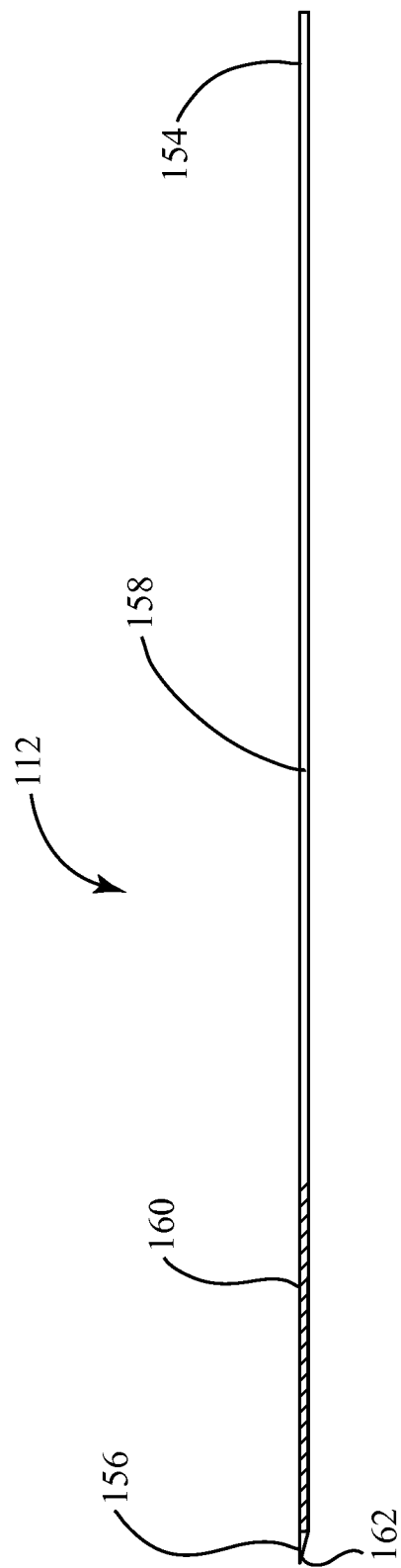

(Proir Art)

APPARATUS FOR BRACHYTHERAPY THAT USES A SCANNING PROBE FOR TREATMENT OF MALIGNANT TISSUE

CROSS REFERENCED TO RELATED APPLICATIONS

This application is related to U.S. Ser. No. 12/834,357, filed concurrently herewith.

BACKGROUND OF THE INVENTION

1. Field of the Invention

This invention relates broadly to ultrasonic medical imaging systems. More particularly, this invention relates to probes and scanning devices used in combination with needle biopsy assemblies and delivery systems for guided biopsy over askew pathways.

2. State of the Art

Ultrasound scanning is an important diagnostic tool used by medical professionals. Medical devices which employ ultrasound scanning are generally categorized as either cavital imaging devices or body imaging devices. Cavital imaging devices, often referred to as probes, are usually inserted into a cavity of the patient to take and capture images of tissue within and adjacent the cavity. Cavital probes are frequently used to provide transvaginal, transesophagual, and transrectal imaging.

Transrectal probes are important for detecting prostate cancer and rectal cancer, especially for men over the age of fifty. If prostate cancer is suspected after a patient has undergone a physical examination or a Prostate Specific Antigens test, then a biopsy is typically performed to collect tissue samples from the prostate for evaluation by a pathologist. As prostate tumors are small growths which can be scattered about different portions of the prostate, multiple tissue samples (e.g., typically between 9 and 18) are usually taken from the prostate during a biopsy procedure. Performing a biopsy procedure involves inserting a transrectal ultrasonic probe into the rectum of the patient, a procedure known as a Transrectal Ultrasound (TRUS) Guided Prostate Biopsy. The probe, in conjunction with imaging software and associated equipment, generates images of two-dimensional slices of the prostate.

Transrectal ultrasonic probes are also used to provide guidance for transperineal procedures including brachytherapy, cryotherapy or transperineal saturation biopsies. All of these procedures involve inserting needles through a grid through the perineum and utilizing the probe for guidance.

The probe includes one or more ultrasonic transducers which generate a narrow pulse of sound which propagates through surrounding tissue and is reflected back to and captured by the transducer. The density of the tissue and its distance from the transducer effects the properties of the return signal or backscatter received by the transducer. In this manner, the properties of the return signal or backscatter can be used to construct an image of the secondary tissue.

Standard ultrasonic probes contain one or more of such ultrasonic transducers mounted inside a hollow tip. The transducer(s) pivot or quickly rotate within the tip (approximately five to ten times per second) to generate and receive pulses at multiple orientations at a given position of the probe. The probe is used to generate longitudinal images (inline with the axis of the probe) and/or transverse images (perpendicular to the axis of the probe tip). This dual axis image capability is referred to as bi-plane imagining. Solid-state probes utilize a plurality of very small transducers aligned in the probe (e.g. columns wrapped around a small portion of the diameter of the probe and along the length of the probe). Instead of pivoting or rotating a single transducer, the solid state probe sequentially pulses a column of the aligned transducers to create a cross sectional image of the tissue of interest. In this manner, the solid-state probe generates dual axis, bi-plane images.

During an ultrasonically guided prostate biopsy procedure, an ultrasonic probe is inserted into the rectum of the patient adjacent the prostate. Images generated by the probe are used to identify the particular portion(s) of the prostate to biopsy, and to properly position the probe, a guide assembly coupled to the probe, and a needle assembly which is advanced though the guide assembly. The guide assembly guides the distal end of the needle assembly through the rectal wall to a fixed position and orientation adjacent the prostate. Additional images generated by the probe during the procedure help the physician monitor and verify the depth and position of the needle assembly within the prostate.

The needle assembly typically includes a wire shaped biopsy needle and an outer cylindrically shaped cannula which receives and supports the biopsy needle. The needle assembly is often coupled to and operably disposed within a spring loaded instrument, typically referred to as a biopsy gun. The biopsy gun is used to advance the needle of the needle assembly into the prostate. During a first firing of the biopsy gun, the needle rapidly advances relative to the cannula into the prostate over a distance called the stroke length, which is typically between 15 mm to 25 mm. A second firing of the biopsy gun causes the cannula to advance over the exposed notch portion of the needle in the prostate. As the cannula advances over the exposed notch portion of the needle, it cuts and severs tissue surrounding the needle and traps the tissue within the notch portion, thus capturing a tissue sample. The needle and cannula are then withdrawn from the patient with the tissue sample captured within the cannula. This process can be repeated at multiple tissue locations in the prostate.

Controlled movement of a transducer over a range of locations within a probe allows for more accurate and complete imaging, and requires less movement or positioning of the probe. U.S. Pat. No. 5,592,942 to Webler discloses an automated longitudinal position translator for ultrasonic imaging probes, and methods of using such probes within a blood vessel. U.S. Pat. No. 6,004,271 to Moore discloses a combined motor drive and automated longitudinal position translator for an ultrasonic imaging system. U.S. Pat. No. 6,200,269 to Lin, et al discloses a forward scanning ultrasound catheter probe which maintains a transducer on a platform at a distal end of the probe and pivots the platform via a piezoelectric drive to create a scanning plane. Controlled translational and rotational movement of a transducer in a transrectal probe is disclosed in U.S. patent application Ser. No. 11/475,674, and illustrated in FIGS. 15A-15 herein.

SUMMARY OF THE INVENTION

The invention is directed to an improved transrectal ultrasonic probe which is preferably utilized in conjunction with a biopsy needle assembly and delivery system similar to those disclosed in U.S. patent application Ser. No. 11/895,228, U.S. patent application Ser. No. 11/475,674, and U.S. patent application Ser. No. 12/834,357, which are herein incorporated by reference in their entireties. The improved probe allows for controlled translational and rotational movement of an ultrasonic transducer inside and across a substantially narrow distal scanning portion of the probes housing. The narrow distal scanning portion of the probes housing facilitates positioning and orienting the probe at different angles within the patient about the prostate, and imaging and biopsying the prostate. Transrectal probes commonly used in the art cause significant discomfort to the patient. The inventors have found that the transrectal probe of application Ser. Nos. 11/895,228 and 11/475,674 also cause discomfort to patients, and that the substantially narrow distal scanning section of the new improved probe reduces this discomfort. The new probe also provides structure that can be used to support and protect the coiled coax carrying the transducer signal data.

The improved probe includes a housing which has a first elongate portion and a second elongate portion proximal of the first elongate portion. The first elongate portion is substantially narrower (e.g., has a substantially smaller cross sectional area) than the second elongate portion and is insertable into the rectum of the patient. The first elongate portion houses an ultrasonic transducer which is capable of emitting acoustic energy and detecting acoustic backscatter signals. The larger second elongate portion houses a platform assembly which is rotatable relative thereto, and movable member which is both rotatable and translatable relative thereto. The platform assembly and movable member are coupled to the transducer by at least one connector extending between the first and second elongate portions of the housing such that rotational movement of the platform assembly within the second elongate portion causes rotation of the transducer within the first elongate portion, and translational movement of the moveable member within the second elongate portion causes translational movement of the transducer within the first elongate portion. The platform assembly preferably includes a transmission system which is selectively operated to convert rotational movement of a proximally situated drive shaft into guided translation of the moveable member relative to the platform assembly along a linear axis. In this manner, the platform assembly and at least one connector together allow for controlled translational and rotational movement of the transducer in the substantially narrower first elongate scanning portion of the housing.

In the preferred embodiment, the first and second elongate portions of the housing are fluidly coupled with each other and filled with a ultrasonic coupling medium (e.g. clear ultrasound transmission gel such as oil which preferably has acoustic properties similar to tissue and water). The first elongate portion of the housing is preferably made from a plastic that allows for transmission of the ultrasonic signals therethrough. Thus, the first elongate portion of the housing and the transmission gel are relatively transparent with respect to ultrasonic signals emitted by the transducer passing therethrough. The oil flows freely between the first and second elongate portions. As a result, movement of the transducer, sled, movable member, connector(s), and platform assembly within the housing causes zero net displacement of the ultrasound coupling medium, which eliminates leakage. The volume of the first and second elongate portions of the probe is fixed. Thus, any change in net displacement of the components within the first and second elongate portions would put pressure on the seals therein, causing oil to leak out of the housing or air to be pulled into the housing, either of which can cause degradation of the image procured from the probe data.

The probe is preferably operable in a first mode for transverse scanning of tissue, and in a second mode for longitudinal scanning of tissue. In the first mode, rotational movement of the drive shaft effectuates rotation (preferably three hundred and sixty degree rotation) of the transducer within the first elongate portion while the transducer remains longitudinally fixed relative to the first elongate portion, thus capturing a transverse image of the tissue relative to the probe axis. In the second mode, rotational movement of the drive shaft effectuates translational movement of the transducer, preferably parallel to the probe axis, through the first elongate portion while the transducer is rotatably fixed relative to the first elongate portion, thus capturing a longitudinal image of the tissue relative to the probe axis.

In the preferred embodiment, a first connector is rigidly coupled to both the transducer and the movable member, and a second connector is rigidly coupled to the frame of the platform assembly and slidably coupled to the transducer. The first connector directly links translational and rotational movement of the movable member to that of the transducer. The second connector rigidly supports the transducer and guides the translation thereof, preferably parallel to the linear axis along which the movable member translates, and reduces undesired movement of the transducer during operation. In this manner, the first and second connectors transfer controlled movement of the movable member and platform assembly to the transducer within the substantially smaller scanning portion of the housing while providing support and stability to the transducer.

In the preferred embodiment, the improved transrectal ultrasonic probe is utilized in conjunction with a biopsy needle assembly for capturing a tissue sample from the prostate of the patient, and a delivery system which includes a guide assembly and a biopsy gun for guiding and forcing the needle assembly into the prostate. The needle assembly includes a flexible biopsy needle and an outer cannula for receiving and supporting the biopsy needle. The needle has a proximal end, a tissue piercing distal end, a sampling section proximal of the tissue piercing distal end, a bending section proximal of the sampling section, and a body portion proximal of the bending section. A cannula with a tissue piercing distal tip surrounds the needle. The cannula has a proximal end, a tissue piercing distal tip, and an elongate body extending between the proximal end and the second tissue piercing distal tip. The elongate body of the cannula includes a bendable portion adjacent the tissue piercing distal tip. The cannula defines a lumen which extends through the elongate body. The biopsy needle is insertable into and longitudinally translatable through the lumen of the cannula.

The guide assembly includes at least one guide channel extending between an inlet and an outlet. The inlet receives the distal end of the needle assembly (e.g., the needle and the cannula). The guide channel functions to physically bend the needle and cannula when the needle and cannula are advanced therethrough such that the distal end of the needle assembly exits the outlet of the guide channel at a desired orientation and direction. In particular, the distal section of the guide channel is curved to provide a bend angle across the distal section. When the needle assembly passes though the bend of the distal section, the distal section bends the needle and cannula such that the needle and cannula are aligned in the bent configuration with the tissue piercing distal ends of the needle and cannula disposed adjacent each other in the desired orientation and direction. In this manner, the needle and cannula are directed by the guide assembly in a predetermined controlled direction to facilitate adequate placement of the sampling section of the needle into the desired tissue to be sampled.

The guide assembly also includes a housing which preferably has a clip section and a curved bottom surface which defines an oval shaped hole. The clip section, curved bottom surface, and hole are constructed to allow the guide assembly to be attached to the improved probe for insertion into the rectum of a patient. In particular, the distal end of the probe is insertable through the oval shaped hole of the guide assembly, and the clip section is attachable to an adjustable guide collar coupled to the probe. The guide collar is movable relative to the probe through various angles and translational distances relative to the probe to position the guide assembly at various locations and orientations relative to the prostate. The probe is operably coupled to a data processing system (e.g., a PC computer with standard display software) which provides location information so that the guide collar and attached guide assembly can be moved manually or by automation to predetermined locations.

During a biopsy procedure, the needle assembly is preferably disposed within and coupled to the biopsy gun. The improved probe is inserted into the rectum of the patient adjacent the prostate and the orientation and position of the guide assembly is adjusted using the guide collar. The improved probe is utilized to capture various two dimensional images of the prostate from the substantially narrow distal scanning portion of the housing, and provide feedback as to the positioning and depth of the guide assembly. Once the probe and guide assembly are properly positioned, the respective distal ends of the needle and cannula are advanced together through the inlet of the guide assembly and are guided to a fixed orientation and direction at the outlet of the guide assembly in which both the needle and cannula bend through an angle of at least forty degrees.

The biopsy gun is then fired to advance the needle into the prostate of the patient. During this first firing, the sampling portion of the needle rapidly advances out of the cannula into the prostate over a stroke length which is preferably approximately equal to the length of the sampling section. A second firing of the biopsy gun causes the cannula to advance over the exposed sampling section of the needle in the prostate, trapping sample tissue therein within the notch/sampling section of the needle between the cannula and the needle. The needle and cannula are then withdrawn from the patient with the tissue sample trapped within the cannula. The guide assembly is then adjusted to a new position and/or orientation on the probe via the guide collar, and the process is repeated as needed.

The improved ultrasonic probe may also be used to provide guidance during transperineal procedures including brachytherapy, chryotherapy or other transperineal saturation biopsies in which the needle is inserted through a grid through the perineum and transrectal images from the probe are used for guidance. Brachytherapy is a minimally invasive treatment that administers radioactive seeds (the size of a grain of rice) directly into the prostate, which allows the ability to use higher doses in the seeds without damaging any surrounding healthy tissue. The radioactive seeds are placed into thin needles and directed into the prostate through the perineum. The seeds release low dose radiation for several weeks or months, killing the cancer cells. Cryotherapy uses argon gas to freeze and helium gas to thaw, a process which destroys cancer cells in the prostate. A warming catheter is inserted through the urethra to protect it during the freezing process of the prostate. The cancer cells in the prostate are destroyed as they thaw. The probe may also be used for guidance during laparascopic and non-laparoscopic surgeries involving other cavities such as the abdominal cavity (e.g., surgeries involving the small intestine, large intestine, stomach, spleen, liver, pancreas, kidneys, and adrenal glands), the thoracic cavity, and the pelvic cavity.

According to one aspect of the invention, the transducer of the probe is supported by a sled, and the sled defines a slot for slidably coupling the sled to a respective guide member and allowing the sled to translate along the respective guide member.

According to yet another aspect of the invention, the platform assembly includes at least one track extending parallel to the linear axis. The movable member is slidably coupled to the track, thus providing guided translation of the movable member.

According to yet another aspect of the invention, the first elongate portion of the housing has a maximum outside diameter of approximately 0.745 inches, preferably between 0.740 inches and 0.750 inches.

Additional objects and advantages of the invention will become apparent to those skilled in the art upon reference to the detailed description taken in conjunction with the provided figures.

BRIEF DESCRIPTION OF THE DRAWINGS

FIG. 7 is a perspective view of the probe of FIG. 1 with a third elongate portion of the housing shown transparent.

FIG. 9 is a broken side view of the biopsy needle of the invention.

FIG. 10A is a side view of the tissue piercing distal end of the biopsy needle of FIG. 9.

FIG. 10B is a longitudinal view of the cross section of the sampling section of the biopsy needle of FIG. 9.

FIG. 10C is a longitudinal view of the cross section of the bending section of the biopsy needle of FIG. 9.

FIG. 10D is a longitudinal view of the cross section of the body portion of the biopsy needle of FIG. 9.

FIG. 11 is a side view of the cannula of the invention.

DETAILED DESCRIPTION OF THE PREFERRED EMBODIMENTS

Figure 1:
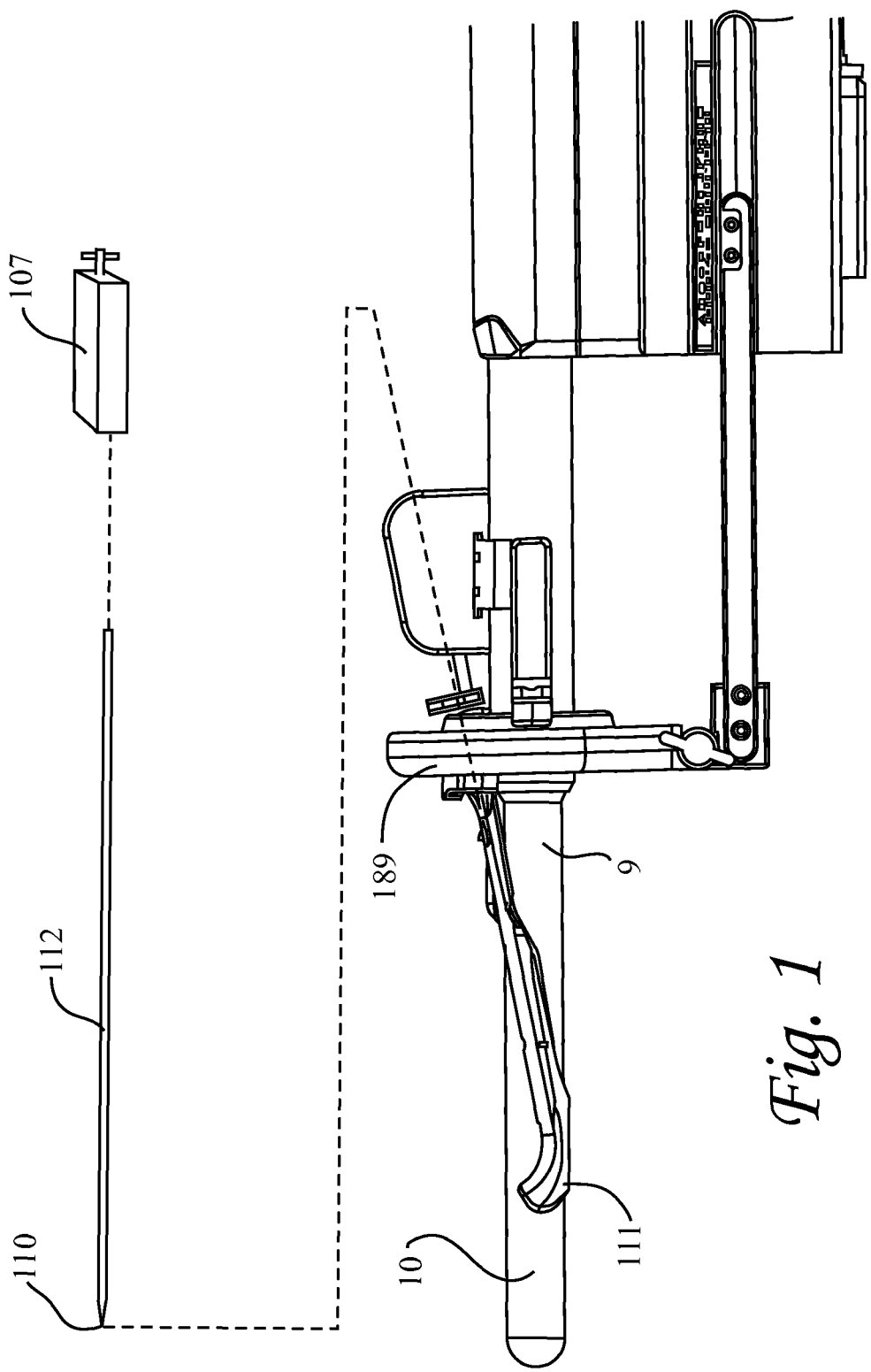
FIG. 1 is a partially exploded view of the preferred embodiment of the probe of the invention used in conjunction with a needle assembly and a biopsy delivery system.

Turning now to FIG. 1, an improved transrectal ultrasonic probe 10 is shown in conjunction with a biopsy needle 110, a cannula 112 for receiving and supporting the biopsy needle 110, and a delivery system which includes a guide assembly 111 for guiding the biopsy needle 110. The needle 110 and cannula 112 are preferably at least partially disposed within and coupled to a biopsy gun 107. The biopsy needle 110, cannula 112, guide assembly 111, and biopsy gun 107 are further discussed below with respect to the operation of these devices in conjunction with the improved probe 10 to capture biopsy tissue samples in a patient.

Figure 2:
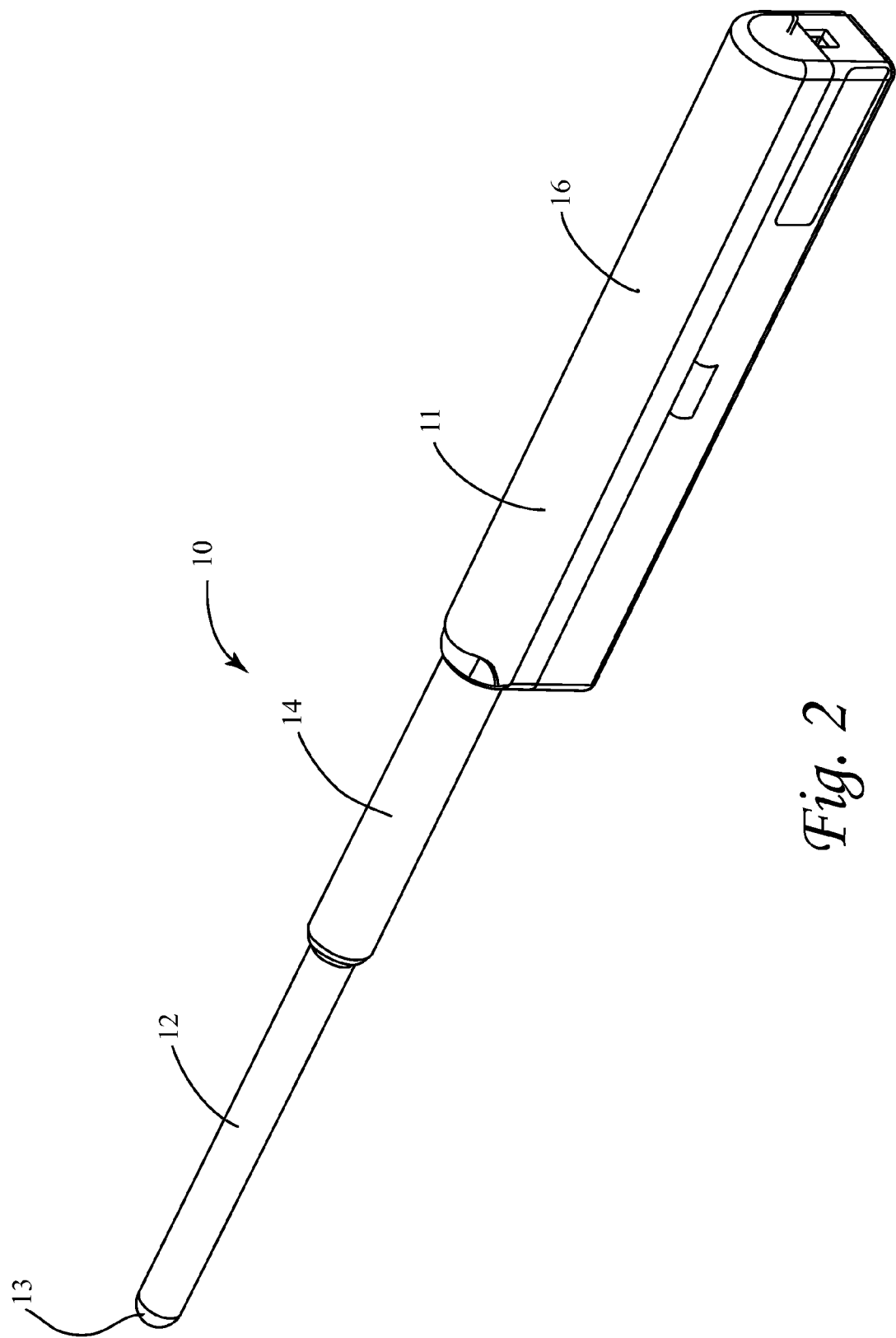
FIG. 2 is a perspective view of the probe of FIG. 1.

The improved probe 10 is best seen with reference to FIGS. 2-7. Turning to FIG. 2, the probe 10 has a housing 11 which includes a first elongate portion 12, a second elongate portion 14 proximal of the first elongate portion, and a third elongate portion 16 proximal of the second elongate portion 14. The first elongate portion 12 is substantially narrower (e.g., has a substantially smaller cross sectional area) than the second elongate portion 14, and preferably has a circular cross section with an outside diameter of approximately 0.745 inches, preferably between 0.740 inches and 0.750 inches. The second elongate portion 14 preferably has a circular cross section with an outside diameter of approximately 1.06 inches, preferably between 0.75 inches and 1.4 inches. The third elongate portion 16 preferably has an outer body width of approximately 1.62 inches, preferably between 1.4 inches and 2.0 inches. The probe 10 also includes a distal end 13 which is preferably spherically shaped with a decreasing cross sectional area in the distal direction to assist with insertion of the probe 10 into a patient. During use, the first elongate portion 12 is inserted into the rectum of the patient with the larger second elongate portion 14 remaining outside of the rectum of the patient.

Figure 3:
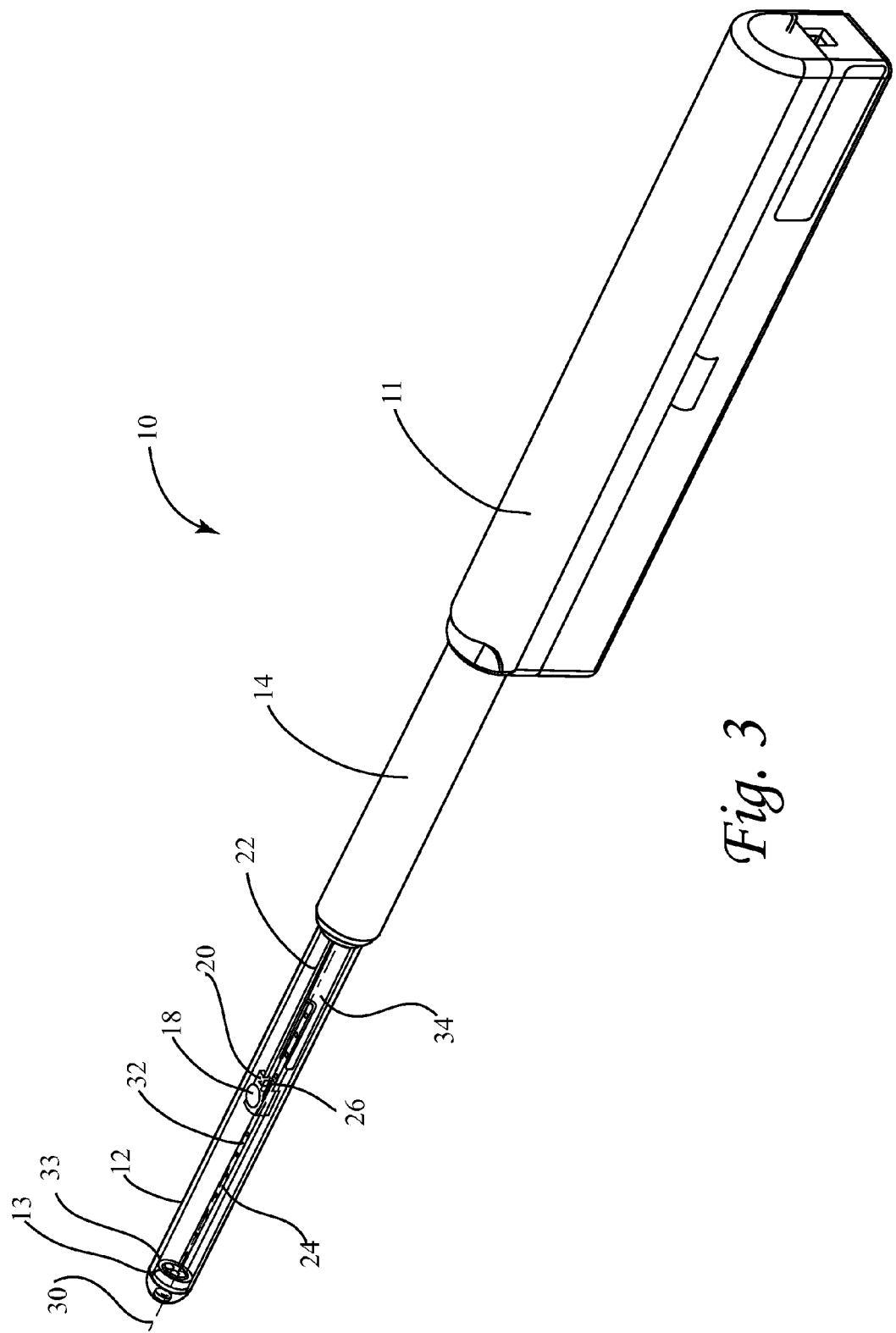
FIG. 3 is a perspective view of the probe of FIG. 1 with a first elongate portion of the housing shown transparent.
Figure 5:
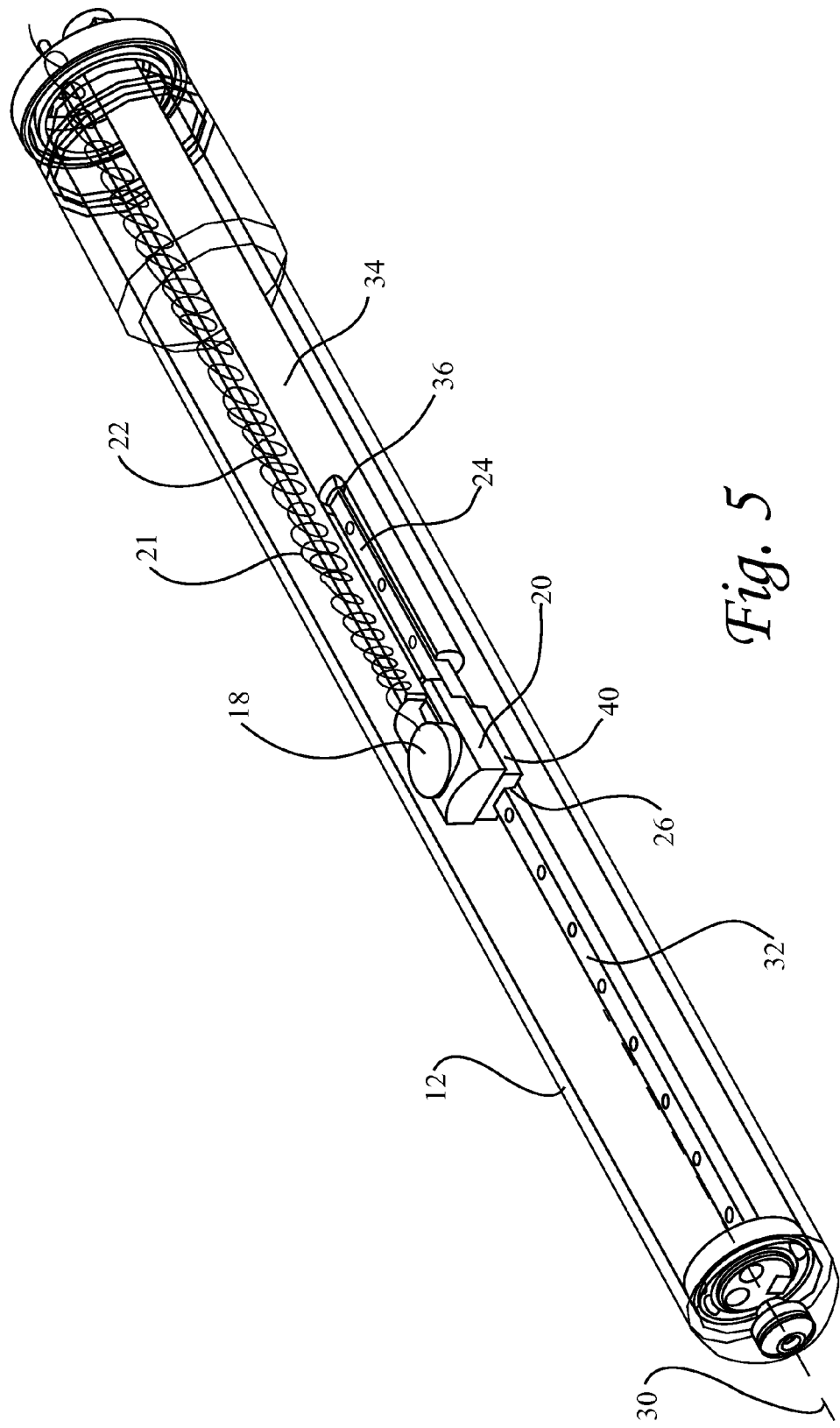
FIG. 5 is an enlarged view of the connectors, sled, and transducer of FIGS. 3 and 4.

Turning to FIGS. 3 and 5, the first elongate portion 12 of the housing 11 houses an ultrasonic transducer 18 which is capable of emitting acoustic energy through the first elongate portion 12 and surrounding body cavity and tissue, and detecting acoustic backscatter signals. The transducer 18 is preferably mounted on a sled 20 which is rigidly coupled to a first connector 22 and slidably coupled to a guide portion 32 of a second connector 24 via a slot 26 defined by the bottom portion of the sled 20. In this configuration, the transducer 18 is longitudinally translatable through the first elongate portion 12, preferably parallel to a central axis 30 extending through the first elongate portion 12.

The first connector 22 translates longitudinally through the first elongate portion 12, and functions to push and pull the transducer 18 distally and proximally along the guide portion 32 of the second connector 24. A coiled coax 21 which carries transducer signal data is preferably wrapped around the first connector 22 as shown. The second connector 24 includes both the guide portion 32 and a support brace 34. The guide portion 32 is preferably made from metal or steel and is rigidly attached to the distal end 13 of the probe 10. The guide portion 32 preferably extends parallel to the central axis 30. The support brace 34 defines a slot 36 (FIGS. 5, 6) for receiving a proximal section of the guide portion 32 and functions to support the guide portion 32. The support brace 34 is made of a plastic material that allows it to deflect to prevent binding thereof when the first elongate portion 12 of the probe 10 is bent. The second connector 24 thus provides a guided pathway for directing longitudinal translation of the sled 20 as well as the transducer 18. The second connector 24 minimizes unwanted movement of the sled 20 and transducer 18. The second connector 24 rigidly maintains the radial position of the sled 20 and transducer 18 relative to the first elongate portion 12 of the housing 11 and provides support to the sled 20 and transducer 18. The first and second connectors 22, 24 extend between the first and second elongate portions 12, 14 of the housing 11, and respectively attach to a movable member and a platform assembly within the second elongate portion 14 as further discussed below with respect to FIGS. 4 and 6.

Figure 4:
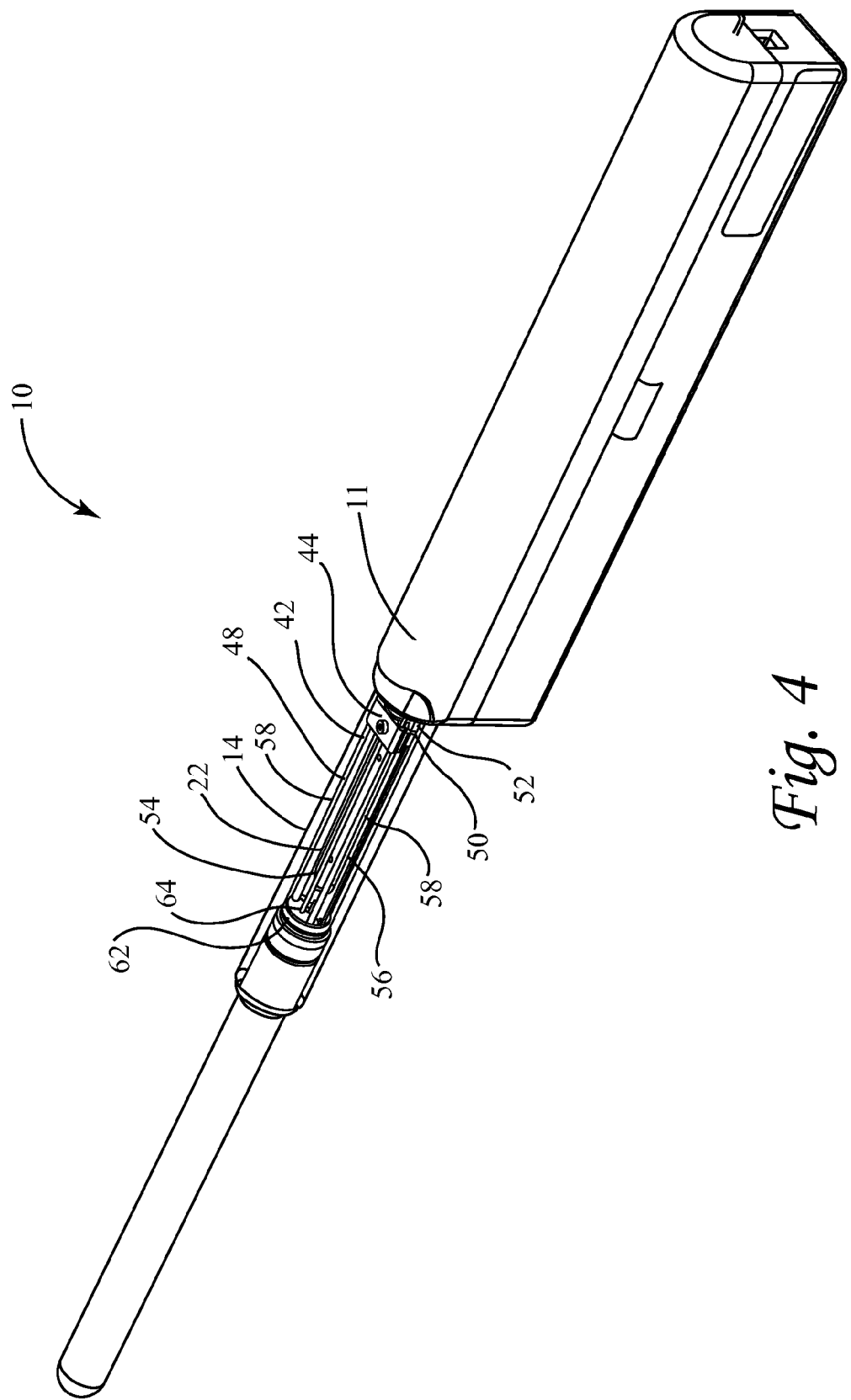
FIG. 4 is a perspective view of the probe of FIG. 1 with a second elongate portion of the housing shown transparent.
Figure 6A:
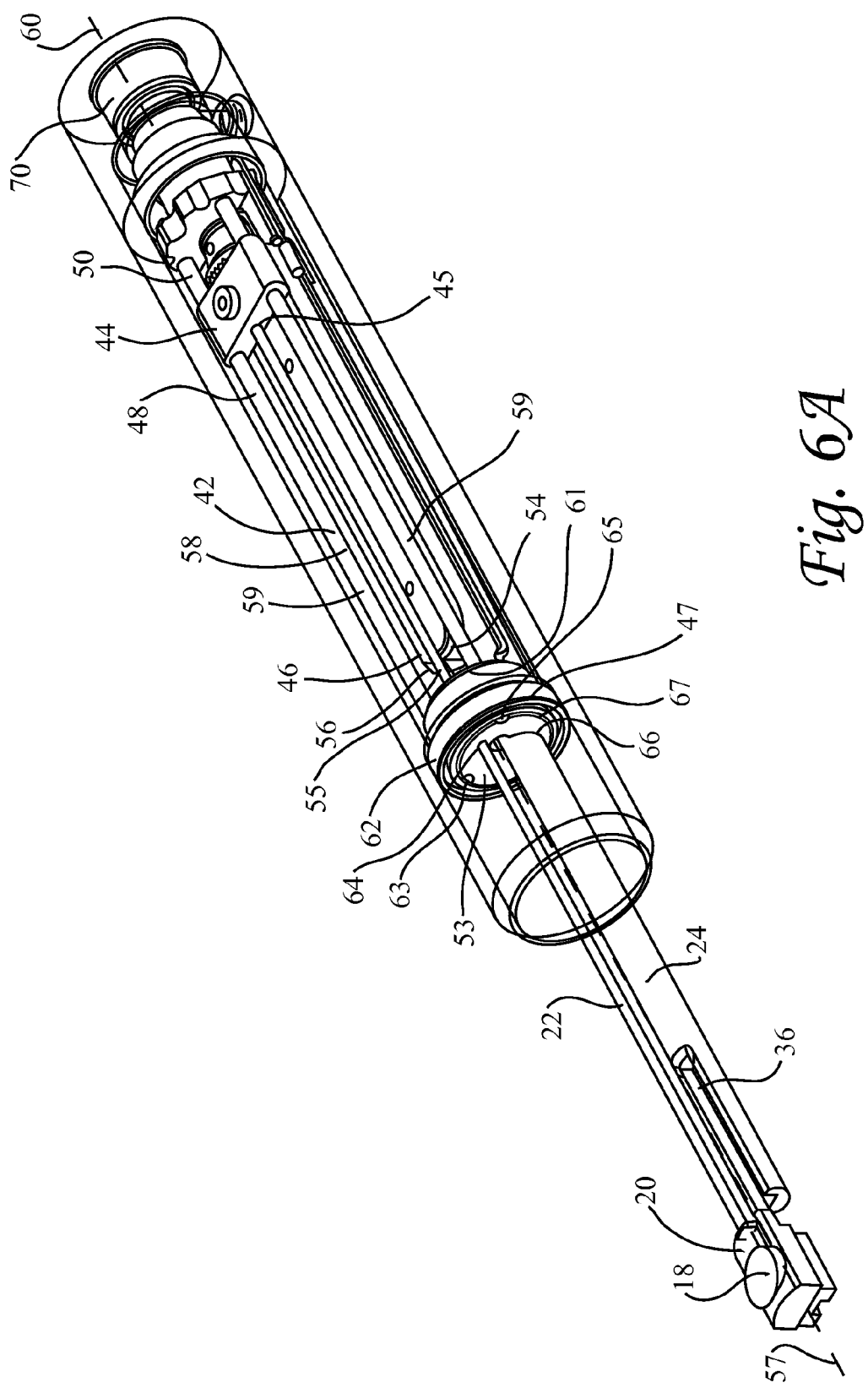
FIG. 6A is an enlarged view of the platform assembly, movable member, connectors, transducer, and sled of FIGS. 3 and 4 without the guide section of the second connector.
Figure 6B:
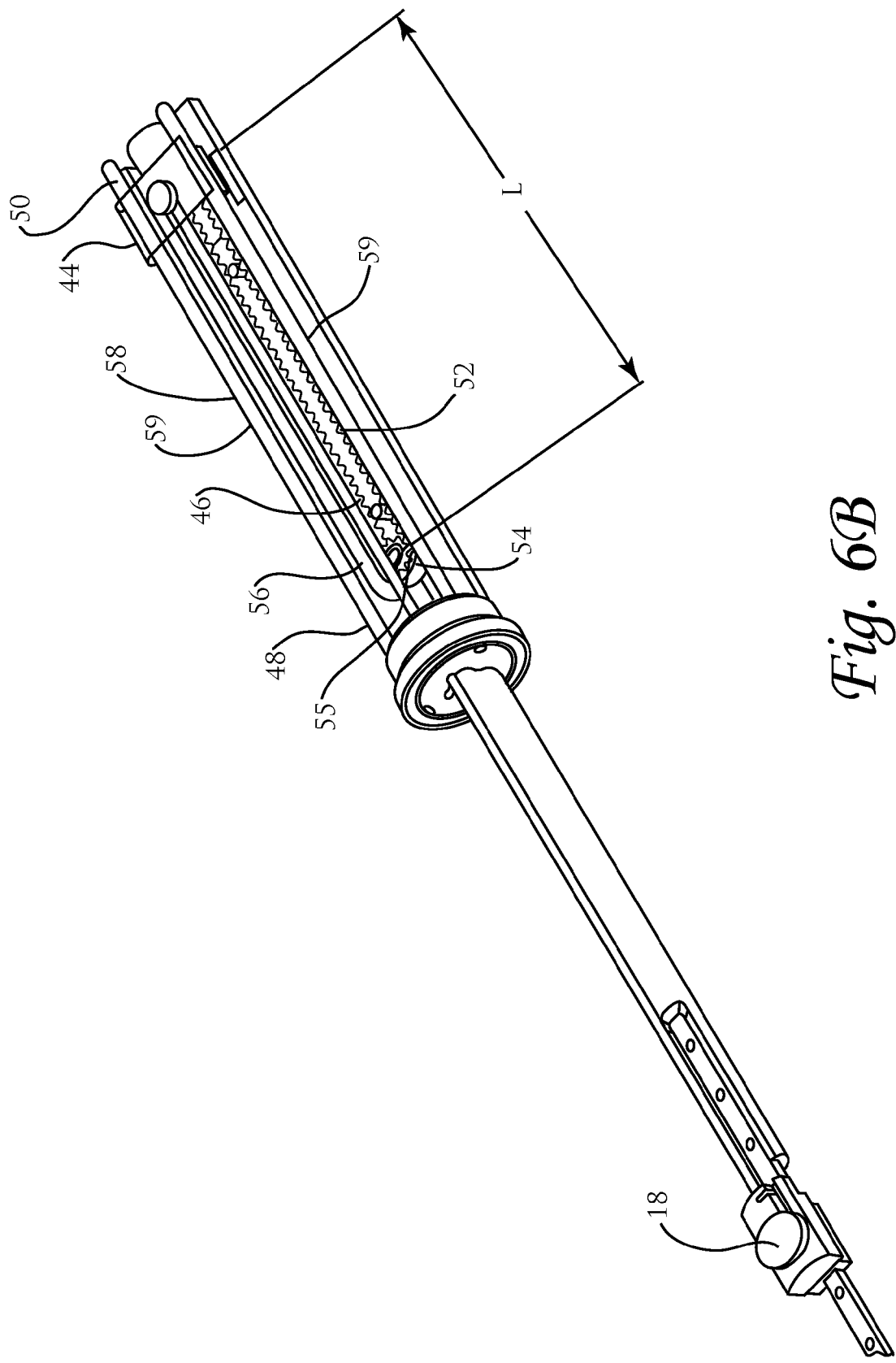
FIG. 6B is an enlarged alternate view of the platform assembly, movable member, connectors, transducer, and sled of FIG. 6A.

Turning now to FIGS. 4, 6A, and 6B, the second elongate portion 14 of the housing 11 houses a platform assembly 42 which is rotatable within and relative to the second elongate portion 14 and longitudinally fixed relative thereto. The platform assembly 42 supports a movable member 44 which translates relative to a frame 48 of the platform assembly 42. The movable member 44 is both rotatable within and relative to the second elongate portion 14, and translatable therethrough. The platform assembly 42, in addition to the frame 48, includes a transmission system 46. The transmission system 46 functions to drive reciprocating proximal and distal translation of the movable member 44 through the second elongate portion 14, and preferably converts rotation of a proximally situated drive shaft (further discussed below) into the translation of the movable member.

In the preferred embodiment, the transmission system 46, best seen in FIG. 6B, includes a vertical bevel gear 50, a horizontal bevel gear 52, a belt pulley 54, a belt 56, and an integral belt pin (not shown). The horizontal bevel gear 52 engages with the vertical bevel gear 50, and the belt 56 and belt pulley 54 rotate with the horizontal bevel gear 52. The integral belt pin is fixed to the belt 56, and is positioned in and slidable through a slot (not shown) on a bottom side of the movable member 44. As the belt pulley 54 rotates, the pin moves with the belt 56 and pulls the movable member 44 along with it. When the pin reaches and traverses one of the proximal (hidden) and distal 55 arced ends of the belt pulley 54, it slides through the slot in the bottom of the movable member 44 and then pulls the movable member 44 in the opposite direction as it circles back with the belt 56 toward the other of the proximal and distal 55 arced ends of the belt pulley 54.

In the preferred embodiment, the frame 48 of the transmission system 46 (best seen in FIG. 6A) includes at least one track 58 which supports the movable member 44 and preferably extends parallel to a linear axis 60 through the second elongate portion 14. The at least one track 58 may include, for example, two parallel beams or rails 59. The movable member 44 is preferably a sled which is slidably coupled to the track 58 of the frame 48 as shown. The frame 48 includes a neck 61 that interfaces to a bearing 62. The bearing 62 includes an outer race 69 which is longitudinally and rotatably fixed relative to the second elongate portion 14 of the housing 11, and an inner race 67 which is rotatable relative to the outer race 69 and second elongate portion 14. The neck 61 includes a plate portion 53 which is preferably situated in an interference fit with the inner race 67 of the bearing 62. The plate portion 53 defines a first hole 64 for slidably receiving the first connector 22, and a second hole 66 for rigidly receiving the second connector 24. The bearing 62 functions to provide support to the frame 48 and first and second connectors 22, 24, and to prevent radial movement thereof relative to the housing 11. The plate portion 53 includes additional holes 63, 65 for allowing the ultrasonic fluid to freely flow between the first and second elongate portions 12, 14. The proximal end of the second elongate portion 14 is sealed so that no fluid flows into the third elongate portion 16. The first connector 22 extends through the hole 64, preferably parallel to the linear axis 60 between the parallel rails 58 of the frame 48, and is rigidly coupled to the movable member 44 at a proximal end 45. The second connector 24 extends through the hole 66, preferably parallel to the linear axis 60, and is rigidly coupled to the neck 61 of the frame 48.

Based on the above arrangement, it will be appreciated that continued rotation of the vertical bevel gear 50, horizontal bevel gear 52, and belt 56 of the transmission system 46 causes reciprocating proximal and distal longitudinal translation of the movable member 44 along a characteristic length L of the track 58 of the frame 48.

It will also be appreciated that the first connector 22 rigidly couples the transducer 18 in the first elongate portion 12 of the housing 11 to the movable member 44 in the second elongate portion 14 of the housing 11, and thus that reciprocating proximal and distal longitudinal translation of the movable member 44 along the characteristic length L caused by the transmission system 46 causes reciprocating proximal and distal longitudinal translation of the transducer 18 within the first elongate portion 12 of the housing 11 along a length equivalent to the length L. The first connector 22 thus has a length which preferably exceeds the characteristic length L, and also which preferably exceeds the longitudinal length of the second elongate portion 12 such that when the movable member 44 is disposed in the proximal-most position in the frame 48 (e.g., FIGS. 4 & 6B), the first connector 22 still extends through the entire second elongate portion 12 and into the first elongate portion. The second connector 24 also preferably has a length which exceeds the characteristic length L as well as the longitudinal length of the second elongate portion. The second connector 24 slidably couples the transducer 18 to the platform assembly 42. Thus, rotation of the entire platform assembly 42 about the central axis thereof 57 in either a clockwise or counterclockwise direction relative to the second elongate portion 14 of the housing 11 drives rotation of the movable member 44 and first and second elongate members 22, 24, which causes the transducer 18 to rotate in the same direction within the first elongate portion 12 about the central axis 57.

As alluded to above, the first and second elongate portions 12, 14 of the housing 11 are fluidly coupled with each other and filled with a ultrasonic coupling medium (e.g., ultrasonic transmission oil) which flows freely between the first and second elongate portions 12, 14. It will be appreciated that movement of the transducer 18, sled 20, movable member 44, connector(s) 22, 24, and platform assembly 42 within the housing 11 will cause zero net displacement of the ultrasound coupling medium, which eliminates changes in pressure in the fixed volume of the first and second elongate portions 12, 14 of the probe and allows rotatable seals disposed on a drive shaft (further discussed below) to maintain the oil within the first and second elongate portions 12, 14 and prevent air from entering therein. If the net displacement of the ultrasound coupling medium within the first and second elongate portions were to change, then the rotatable seals could fail, causing leakage to occur and potentially causing deterioration of the quality of the image generated from the probe 9.

Turning to FIG. 7, the third elongate portion 16 of the housing 11 can function as a handle for manual operation of the probe 10, or can be grasped by a stand for automated operation thereof. In the preferred embodiment, the third elongate portion 16 houses a motor, clutch, brake, and control circuitry for driving the rotation of two coaxial drive shafts coupled to the frame 48 and the transmission system 46 of the platform assembly 42 in order to selectively rotate and translate the transducer 18 as further discussed below. As shown, the third elongate portion 16 preferably houses a single motor 68 which rotatably drives an inner drive shaft 70. The inner drive shaft 70 extends from the motor 68 through the third elongate portion 16 of the housing 11 to the proximal end of the second elongate portion 14 where it is rotatably coupled to the vertical bevel gear 50 of the transmission system 46 (FIGS. 6A, 6B). The inner shaft 70 thus linearly and reciprocally drives the movable member 44. An electrically controlled clutch 72 is mounted about the inner shaft 70 within the third elongate portion 16, and an outer shaft 74 extends from the clutch 72. The outer shaft 74 is hollow and surrounds the inner shaft 70, which extends through it. The outer shaft 74 extends from the clutch 72 through the third elongate portion 16 of the housing 11 to the proximal end of the second elongate portion 14 where it is rotatably fixed to the frame 48 of the platform assembly 42. An electrically controlled brake 76 is mounted about the outer shaft 74 within the third elongate portion 16 forward of the clutch 72, and is operable to prevent rotation of the outer shaft 74

The clutch 72 and brake 76 operate under control of electrical signals supplied by a motor control processor unit (MCPU). The MCPU can issue a signal which engages or disengages the clutch 72 and brake 76. When the clutch 72 is engaged, it locks (rotatably fixes) the inner and outer shafts 70, 74 to each other such that the outer shaft 74 is rotated by the rotation of the inner shaft 70. As the outer shaft 74 is rotatably fixed to the frame 48 of the platform assembly 42, when the clutch 72 is engaged and the brake is disengaged, rotation of the inner shaft 70 by the motor 68 drives rotation of the outer shaft 74 and the entire platform assembly 42 about its central axis 30 without operating the transmission system 46. When the clutch 72 is unengaged and the brake is engaged, rotation of the inner shaft 70 by the motor 68 operates the transmission system 46 as the inner shaft 70 rotates relative to the outer shaft 74.

The probe 10 preferably includes an outer shaft encoder (not shown) and an inner shaft encoder 71 for monitoring the longitudinal and rotational position of the transducer 18. The encoders each include a wheel which rotates with a respective shaft, and a sensor which monitors the rotational position of the wheel as known in the art. The encoders send signals to the MCPU 73 indicative of the longitudinally and rotational position of the transducer 18. Rotational and positional feedback allow for accurate positioning and rotation of the probe 10 by the physician.

Figure 8:
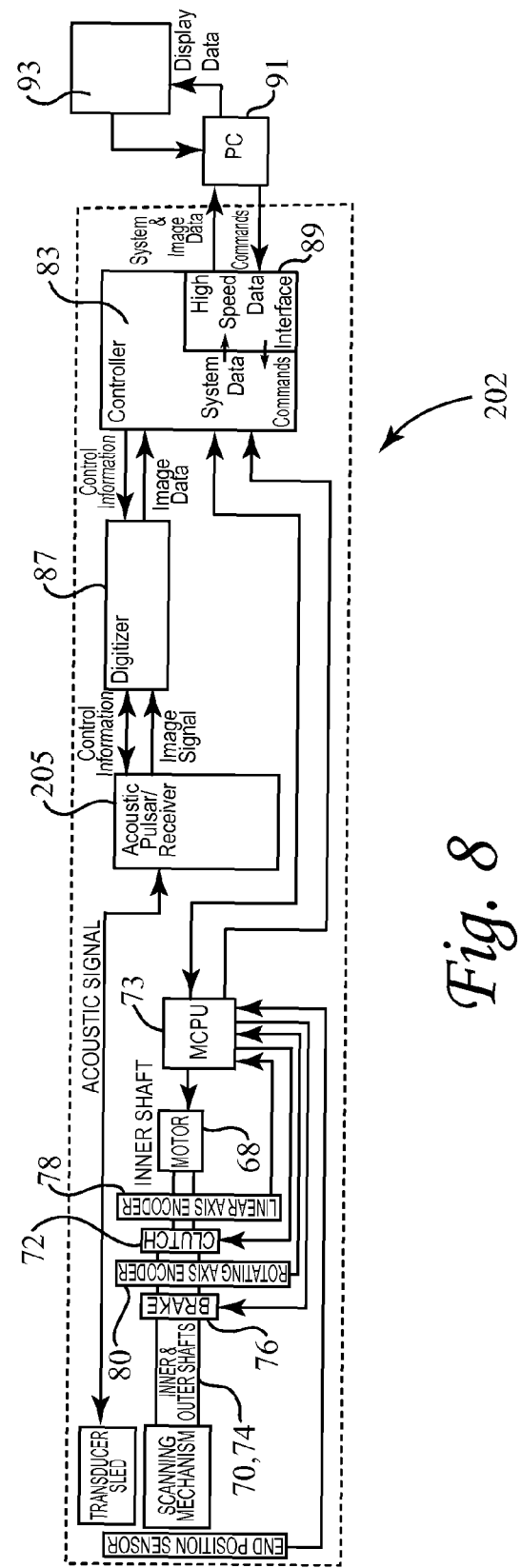
FIG. 8 is a block diagram of the single motor scanning probe and circuit board of the integrated electronics of the probe assembly of the invention.
Figure 12A:
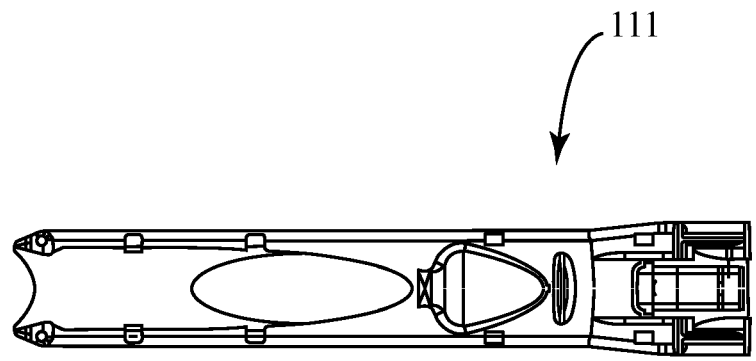
FIG. 12A is a top view of the guide assembly of the invention.
Figure 12B:
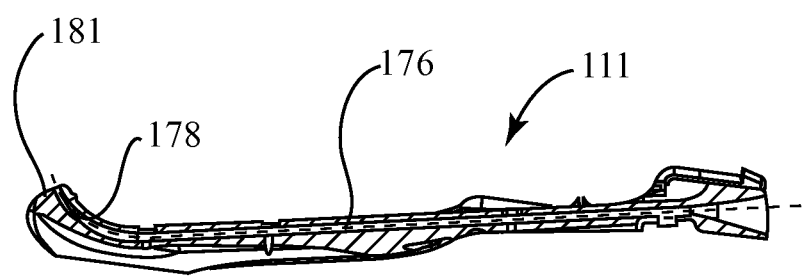
FIG. 12B is a side view of the guide assembly of FIG. 12A.

Turning to FIG. 8, the clutch 72 and brake 76 are controlled by a motion control processing unit (MCPU) 73. The MCPU 73 is operatively connected to a control box or PC. In response to operation command signals received from the control box or PC, the MCPU 73 engages and disengages the clutch 72 and brake 76 to allow for rotational and reciprocal motion of the transducer 18 in the second elongate portion 14. Thus, to move the transducer 18 linearly along the guide 32 of the second connector 24, the clutch 72 is released and the brake 76 is applied. Conversely, to rotate the transducer 18 about the central axis 57 of the platform assembly 42, the clutch 72 is engaged and the brake 76 is released. Thus, when a physician activates the probe 10 using the control box or PC, the MCPU 73 will signal the clutch 72 and brake 76 to engage or disengage depending on the commands initiated by the physician.

The circuitry and electronics of the probe 10 preferably include a controller 83, a pulser/receiver 205, a digitizer 87, and a high speed data interface 89. The controller 83 receives commands from an external data processing system (e.g., a PC computer) 91 having a touch screen display 93 or other control dials and buttons via the data interface 89. These commands are used to configure both the pulser/receiver 85 and the probe 10. An acoustic pulse is generated in the pulser/receiver 85 and sent to the scanning probe 10 over a coaxial cable. Backscattered ultrasound data from the probe transducer 18 is processed by the receiver 85. The data is then digitized by the digitizer 87 and sent to a memory buffer in the controller 83. The data is then sent to the PC 91 for image formation on the touch screen display 93 via the data interface 89.

In response to operation command signals representing a first mode of operation received from the PC 91 via the high speed data interface 89, the controller 83 engages the clutch 72 and disengages the brake 76 to allow for rotational motion of the transducer 18 in the first elongate portion 12 while the transducer 18 remains longitudinally fixed relative thereto (the transmission 46 is inoperable because the inner shaft 70 is rotatably fixed to the outer shaft 74). In response to operation command signals representing a second mode of operation received from the PC 91, the controller 83 disengages the clutch 72 and engages the brake 76 to allow for reciprocating translation of the transducer 18 in the first elongate portion 12 while precluding rotation of it relative thereto (the inner shaft 70 is disengaged from the outer shaft 74 and drives the transmission 46, and the outer shaft 74 is prevented from rotating, which prevents rotation of the platform assembly 42 which is rotatably fixed to the outer shaft 74, and hence the transducer 18, which is rotatably fixed to the platform assembly 42). The controller 83 receives information on the position of the transducer 18 from a position tracker (not shown), which is connected to the probe's rotational axis encoder and linear axis encoder. Various embodiments of the electronics driving operation of the probe 10 can be utilized, including all of those disclosed in U.S. patent application Ser. No. 11/475,674 which has been incorporated herein by reference.

The improved probe 10 allows for controlled translational and rotational movement of the ultrasonic transducer 18 inside and across the substantially narrow distal scanning portion 12 of the probe's housing 11. The narrow distal scanning portion 12 facilitates positioning and orienting of the probe 10 at different angles within the patient about the prostate, and imaging and biopsying the prostate as discussed below. While two connectors are preferred for connecting to the transducer 18 to facilitate translation and rotation thereof, it will be appreciated that a single connector may be utilized which rigidly couples the transducer 18 to the movable member 44, provided that such single connector is sufficiently rigid to firmly maintain the radial position of the transducer 18 relative to the first elongate portion 12 of the housing 11 (e.g. provided the single connector does not bend). It is noted that a single connector should not be directly fixed to the frame 48 of the platform assembly 42 as it would need to translate with the movable member 44 relative to the frame 48. For example, the first connector 22 is sufficient to provide the aforementioned controlled movement to the transducer 18 without guide 32 and support 34 of the second connector 24 provided that the first connector 22 is fixed at both ends to the transducer 18 and movable member 44, does not bend, and will not bend over repeated use of the probe 10.

The improved transrectal ultrasonic probe 10 may be used in conjunction with various biopsy needles and delivery systems known in the art, including, for example, those disclosed in U.S. patent application Ser. Nos. 11/895,228 and 11/475,674, which are herein incorporated by reference in their entireties.

The preferred biopsy needle 110 and cannula 112 to be used in conjunction with the improved probe 10 are best seen with reference to FIGS. 9-11. As most clearly shown in FIGS. 9-10D, the needle 110 includes a proximal end 114, a tissue piercing distal end 116, a sampling section 118 proximal of the tissue piercing distal end 116 and having a flat top surface 124, rounded bottom surface 126, and ground down rounded edges 128, 130 on opposite sides of the top surface 124, a bending section 120 proximal of the sampling section 118 and preferably having a circular cross section, and a body portion 122 proximal of the bending section 120. The sampling section 118, bending section 120, and body portion 122 of the needle 110 are all preferably solidly and integrally formed with varying degrees of flexibility. The bending section 120 is preferably the most flexible portion of the needle 110.

The improved probe 10 may be used in conjunction with the needle 110, cannula 112, and guide assembly 111 in accordance with the biopsy procedure described in U.S. patent application Ser. No. 12/834,357. Alternatively, it will be appreciated that various other methodologies, embodiments, and additional equipment may be utilized with the improved probe 10 to procure a biopsy sample, including, for example, the methodologies, embodiments, and additional equipment described in U.S. patent application Ser. No. 11/895,228.

Figure 13:
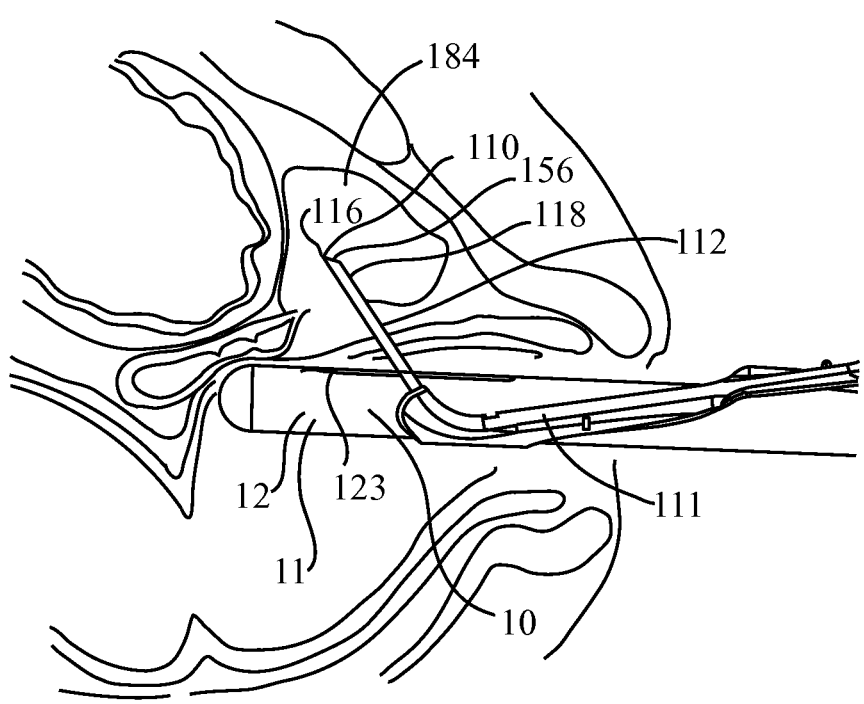
FIG. 13 is a schematic view of the biopsy needle, cannula, and guide assembly mounted on the first elongate portion of the probe of FIG. 1 and used to biopsy the prostate of a patient.
Figure 14A:
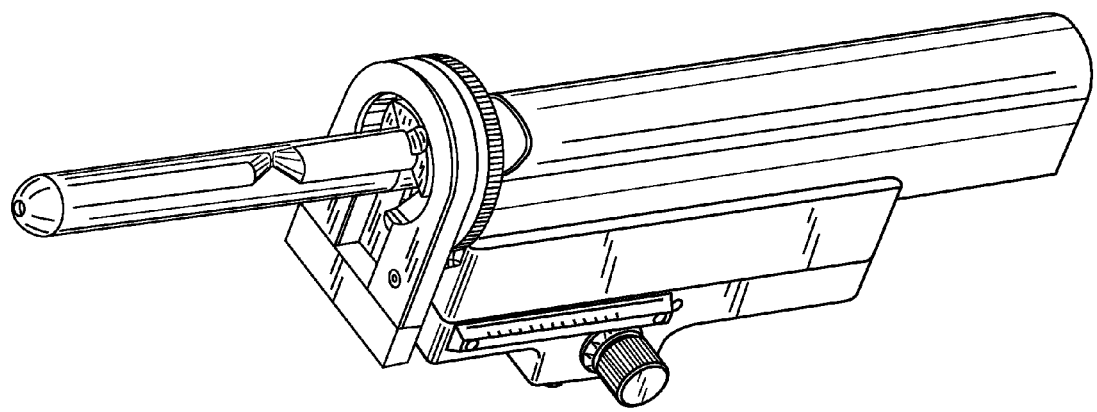
FIG. 14A is a perspective view of an ultrasonic probe known in the art.
Figure 14B:
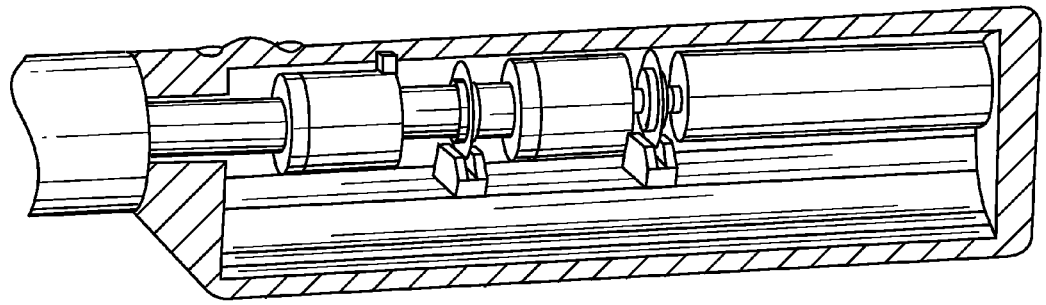
FIG. 14B is a side partially sliced view of a drive assembly known in the art.
Figure 14C:
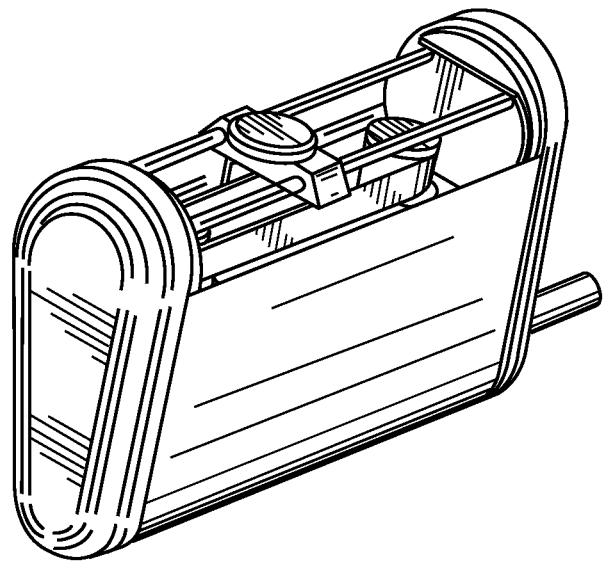
FIG. 14C is a perspective view of a platform assembly and movable member known in the art.
Figure 14D:
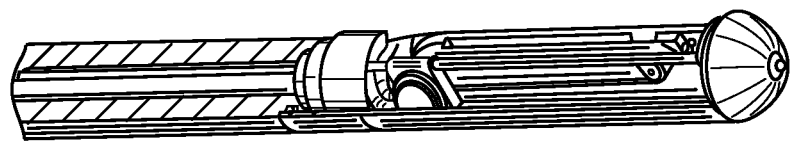
FIG. 14D is a cutaway view disclosing operative components of an ultrasonic probe known in the art.

Turning to FIGS. 1 and 13, the improved ultrasonic probe 10 and needle assembly (e.g. needle 110 and cannula 112) are used with a delivery system which includes the guide assembly 111 and a biopsy gun 107 to procure a tissue sample from the prostate 184 of a patient. The needle 110 and cannula 112 are preferably at least partially disposed within and coupled to the biopsy gun 107. The narrow elongate distal scanning portion 12 of the improved probe 10 is inserted into the rectum of the patient adjacent the prostate 184 as shown in FIG. 14. As discussed above, the substantially small scanning portion 12 of the housing 11 facilitates insertion into the rectum, and positioning and orienting the probe 10 therein. Transrectal probes commonly used in the art cause significant discomfort to the patient, and the inventors have found that the transrectal probe of application Ser. Nos. 11/895,228 and 11/475,674 also cause discomfort to patients. The substantially narrow distal scanning section 12 of the new improved probe 10 reduces this discomfort.

The guide assembly 111 is preferably attached to a guide/index collar 189 (FIG. 1) of the probe 10. The guide/index collar 189 controls radial and axial movement of the guide assembly 111 on the probe 10, and preferably orients the guide assembly 111 such that it straddles the probe 110 adjacent an imaging window 123 in the probe 10, and is sloped slightly downward at a ten degree angle. Alternatively, the guide assembly 111 may be fixed to the probe 110 and/or oriented horizontally relative thereto. Ultrasonic images of the prostate 184 are received through the imaging window 123, unobstructed by the guide assembly 111.

Once the probe 10 and guide assembly 111 are properly positioned within the patient, the respective distal ends 116, 156 of the needle 110 and cannula 112 are advanced together through the inlet 75 of the guide assembly 111 and are guided to a fixed orientation and direction at the outlet 181 of the guide assembly 111 to place the needle 110 and cannula 112 in a bent configuration within the patient adjacent the prostate.

Once the needle 110 and cannula 112 are in a bent configuration and the respective distal ends 116, 156 of the needle 110 and cannula 112 are disposed adjacent the prostate 184, the biopsy gun 107 is fired to advance the needle 110 from the bent configuration into the prostate 184 of the patient. During this first firing, the sampling portion 118 of the needle 110 rapidly advances out of the cannula 112 into the prostate over a stroke length which is preferably approximately equal to the length of the sampling section 118. A second firing of the biopsy gun 107 causes the cannula 112 to fire and advance over the exposed sampling section 118 of the needle 110 in the prostate 184, capturing sample tissue therein between the cannula 112 and the needle 110.

The needle 110 and cannula 112 are then withdrawn from the patient with the tissue sample captured within the cannula 12, and the process is repeated as needed with the improved probe 10 remaining in the patient. It will be appreciated that the narrower distal elongate portion 12 of the housing 11 of the new probe 10 allows for easier manipulation inside of the patient to different positions and orientations.

It will also be appreciated that various biopsy guns, needles, cannulas, delivery mechanisms, and guide assemblies may be utilized in conjunction with the improved probe 10. The improved ultrasonic probe may also be used to provide guidance during transperineal procedures including brachytherapy, chryotherapy or other transperineal saturation biopsies in which the needle is inserted through a grid through the perineum and transrectal images from the probe are used for guidance.

Brachytherapy is a minimally invasive treatment that administers radioactive seeds (the size of a grain of rice) directly into the prostate, which allows the ability to use higher doses in the seeds without damaging any surrounding healthy tissue. The radioactive seeds are placed into thin needles and directed into the prostate through the perineum. The seeds release low dose radiation for several weeks or months, killing the cancer cells. Cryotherapy uses argon gas to freeze and helium gas to thaw, a process which destroys cancer cells in the prostate. A warming catheter is inserted through the urethra to protect it during the freezing process of the prostate. The cancer cells in the prostate are destroyed as they thaw.

The probe may also be used for guidance during laparascopic and non-laparoscopic surgeries involving other cavities such as the abdominal cavity (e.g., surgeries involving the small intestine, large intestine, stomach, spleen, liver, pancreas, kidneys, and adrenal glands), the thoracic cavity, and the pelvic cavity, or during surgeries involving other tissue or joints in the body.

There have been described and illustrated herein several embodiments of an improved ultrasonic probe for use in biopsying tissue in a patient. While particular embodiments of the invention have been described, it is not intended that the invention be limited thereto, as it is intended that the invention be as broad in scope as the art will allow and that the specification be read likewise. Thus, while particular dimensions, shapes, connectors, transmission systems, frames, and means for mounting the transducer and movable member have been disclosed, it will be appreciated that other dimensions, shapes, connectors, transmission systems, frames, and means for mounting the transducer and movable member may be utilized. In addition, while a single motor is disclosed in conjunction with a specific type of drive mechanism, it will be appreciated that multiple motors and other drive mechanisms can be utilized. Moreover, while multiple connectors are disclosed for coupling a transducer in a first elongate portion of the housing with a movable member within a second elongate portion of the housing, it will be appreciated that a single, preferably substantially rigid connector may be utilized instead. While particular configurations of a needle, cannula, guide assembly, and a biopsy delivery system which includes an improved probe and a biopsy gun have been disclosed, it will be appreciated that other configurations may be utilized. Also, while the needle, cannula, and improved probe have been disclosed for biopsying the prostate of a patient, it will be recognized that that the needle, cannula, and improved probe can be used for biopsying tissue of other organs or other parts of the body and that the improved probe may be inserted through other cavities in the body and utilized for guiding other procedures such as brachytherapy, chryotherapy and saturation biopsies. It will therefore be appreciated by those skilled in the art that yet other modifications could be made to the provided invention without deviating from its spirit and scope as claimed.

What is claimed is:

1. An apparatus for ultrasonic imaging of tissue within a body cavity, the apparatus comprising:

a housing having a first elongate portion and a second elongate portion proximal of said first elongate portion, said first elongate portion insertable into the body cavity;

an ultrasonic transducer operably disposed within said first elongate portion and capable of emitting acoustic energy therefrom and detecting acoustic backscatter signals;

a platform assembly operably disposed within said second elongate portion and supporting a moveable member operably disposed within said second elongate portion, said platform assembly providing guided translation of said moveable member relative to said platform assembly along a linear axis, and said platform assembly together with said moveable member being rotatable relative to said second elongate portion;

at least one connector extending between said first elongate portion and said second elongate portion and coupling said ultrasonic transducer to said platform assembly and to said movable member such that rotational movement of said platform assembly within said second elongate portion effectuates rotation of said ultrasonic transducer within said first elongate portion, and translational movement of said moveable member within said second elongate portion effectuates translational movement of said ultrasonic transducer within said first elongate portion; and said housing has a third elongate portion proximal of said second elongate portion, and said apparatus further comprises a drive shaft extending through said third elongate portion of said housing and operably coupled to said platform assembly for effectuating rotation of said ultrasonic transducer relative to said housing in a first mode of operation for transverse scanning of the tissue, and translation of said ultrasonic transducer relative to said housing in a second mode of operation for longitudinal scanning of the tissue; wherein said platform assembly includes a transmission system for converting rotational movement of said drive shaft to translation of said moveable member relative to said platform assembly along said linear axis;

said transmission system includes a plurality of gears configured such that continued rotation of said drive shaft in either a clockwise or counterclockwise direction causes reciprocating proximal and distal longitudinal translation of said movable member and said ultrasonic transducer relative to said housing;

said drive shaft includes an outer drive shaft fixed to said platform assembly and an inner drive shaft extending through said outer drive shaft, selectively rotatable fixed to said outer drive shaft, and mechanically coupled to said plurality of gears of said transmission system, and said inner drive shaft is rotatable fixed to said outer drive shaft and incapable of longitudinally translating said movable member and said ultrasonic transducer relative to said housing in said first mode of operation for transverse scanning of the tissue, and said inner drive shaft is rotatable relative to said outer drive shaft to longitudinally translate said movable member and said ultrasonic transducer relative to said housing in said second mode of operation for longitudinal scanning of the tissue;

an electrically controlled clutch is operably disposed within said third elongate portion of said housing, said clutch being configurable to an engaged position to rotatable fix said inner drive shaft to said outer drive shaft for operation of said apparatus in said first mode, and to an unengaged position to allow rotation of said inner drive shaft relative to said outer drive shaft for operation of said apparatus in said second mode;

an electrically controlled brake operably is disposed within said third elongate portion of said housing, and said brake is configurable to an engaged position to prevent rotation of said outer drive shaft and said platform assembly relative to said housing when said clutch is unengaged in said second mode of operation, and to an unengaged position to allow rotation of said outer drive shaft and said platform assembly when said clutch is engaged in said first mode of operation; and said at least one connector includes a first connector which rigidly couples said ultrasonic transducer to said movable member, and a second connector which defines a guide slidably coupled to said ultrasonic transducer and a support portion fixed to said platform assembly.

2. An apparatus according to claim 1, wherein:
rotational movement of said platform assembly effectuates rotation of said ultrasonic transducer while said ultrasonic transducer is longitudinally fixed relative to said first elongate portion in said first mode of operation for transverse scanning of the tissue; and
translational movement of said moveable member effectuates translational movement of said ultrasonic transducer while said ultrasonic transducer is rotatably fixed relative to said first elongate portion in said second mode of operation for longitudinal scanning of the tissue.

3. An apparatus according to claim 1, wherein:
said ultrasonic transducer is supported by a sled, and said sled defines a slot for receiving said guide of said second connector and allowing said sled and said ultrasonic transducer to translate along said guide.

4. An apparatus according to claim 3, wherein:
said second connector is made from a flexible plastic.

5. An apparatus according to claim 1, wherein:
said first connector extends parallel to said linear axis.

6. An apparatus according to claim 1, wherein:
said second connector extends parallel to said linear axis.

7. An apparatus according to claim 1, wherein:
said platform assembly includes at least one track, and said movable member is slidably coupled to said at least one track.

8. An apparatus according to claim 7, wherein:
said at least one track includes two parallel rails coupled to said movable member and extending parallel to said linear axis.

9. An apparatus according to claim 8, wherein:
said at least one connector includes a first connector which rigidly couples said ultrasonic transducer to said movable member, and a second connector which defines a guide slidably coupled to said transducer and a support fixed to said platform assembly, and a portion of said first connector extends in parallel between said two parallel rails.

10. An apparatus according to claim 1, wherein:
said first elongate portion of said housing has a maximum diameter in a range of 0.740 inches to 0.750 inches.

11. An apparatus according to claim 1, wherein:
rotation of said inner drive shaft causes rotation of said platform assembly about a central longitudinal axis extending through said platform assembly in said first mode of operation.

12. An apparatus according to claim 1, further comprising:
a motor operably disposed within said third elongate portion of said housing and mechanically coupled to said inner drive shaft.

13. An apparatus according to claim 1, wherein:
said first elongate portion has a first cross sectional area, and said second elongate portion has a second cross sectional area which is larger than said first cross sectional area.

14. An apparatus according to claim 1, wherein:
said movable member is translatable along a characteristic length, and said at least one connector is longer than said characteristic length.

15. An apparatus according to claim 14, wherein:
said second elongate portion has a longitudinal length which is greater than said characteristic length, and said at least one connector is longer than said longitudinal length.

16. A system for biopsying tissue of a patient, the system comprising:
a guide assembly which defines at least one guide channel for receiving, guiding, and orienting a needle and a cannula through said guide assembly to a desired orientation and position for biopsying the tissue of the patient; and an ultrasonic probe for taking ultrasonic images of the tissue inside the patient, said probe including
(i) a housing having a first elongate portion and a second elongate portion proximal of said first elongate portion, said first elongate portion having a first cross sectional area and insertable into a body cavity, said second elongate portion having a second cross sectional area larger than said first cross sectional area;
(ii) an ultrasonic transducer operably disposed within said first elongate portion and capable of emitting acoustic energy therefrom and detecting acoustic backscatter signals;
(iii) a platform assembly operably disposed within said second elongate portion and supporting a moveable member operably disposed within said second elongate portion, said platform assembly providing guided translation of said moveable member relative to said platform assembly along a linear axis, and said platform assembly together with said moveable member rotatable relative to said second elongate portion;
(iv) at least one connector extending between said first elongate portion and said second elongate portion and coupling said ultrasonic transducer to said platform assembly and to said movable member such that rotational movement of said platform assembly within said second elongate portion effectuates rotation of said ultrasonic transducer within said first elongate portion, and translational movement of said moveable member within said second elongate portion effectuates translational movement of said ultrasonic transducer within said first elongate portion; and
(v) said housing has a third elongate portion proximal of said second elongate portion, and said apparatus further comprises a drive shaft extending through said third elongate portion of said housing and operably coupled to said platform assembly for effectuating rotation of said ultrasonic transducer relative to said housing in a first mode of operation for transverse scanning of the tissue, and translation of said ultrasonic transducer relative to said housing in a second mode of operation for longitudinal scanning of the tissue; wherein said platform assembly includes a transmission system for converting rotational movement of said drive shaft to translation of said moveable member relative to said platform assembly along said linear axis;

said transmission system includes a plurality of gears configured such that continued rotation of said drive shaft in either a clockwise or counterclockwise direction causes reciprocating proximal and distal longitudinal translation of said movable member and said ultrasonic transducer relative to said housing;

said drive shaft includes an outer drive shaft fixed to said platform assembly and an inner drive shaft extending through said outer drive shaft, selectively rotatably fixed to said outer drive shaft, and mechanically coupled to said plurality of gears of said transmission system, and said inner drive shaft is rotatably fixed to said outer drive shaft and incapable of longitudinally translating said movable member and said ultrasonic transducer relative to said housing in said first mode of operation for transverse scanning of the tissue, and said inner drive shaft is rotatable relative to said outer drive shaft to longitudinally translate said movable member and said ultrasonic transducer relative to said housing in said second mode of operation for longitudinal scanning of the tissue;

an electrically controlled clutch is operably disposed within said third elongate portion of said housing, said clutch being configurable to an engaged position to rotatably fix said inner drive shaft to said outer drive shaft for operation of said apparatus in said first mode, and to an unengaged position to allow rotation of said inner drive shaft relative to said outer drive shaft for operation of said apparatus in said second mode;

an electrically controlled brake operably is disposed within said third elongate portion of said housing, and said brake is configurable to an engaged position to prevent rotation of said outer drive shaft and said platform assembly relative to said housing when said clutch is unengaged in said second mode of operation, and to an unengaged position to allow rotation of said outer drive shaft and said platform assembly when said clutch is engaged in said first mode of operation; and said at least one connector includes a first connector which rigidly couples said ultrasonic transducer to said movable member, and a second connector which defines a guide slidably coupled to said ultrasonic transducer and a support portion fixed to said platform assembly.

17. A system according to claim 16, wherein:
rotational movement of said platform assembly effectuates rotation of said ultrasonic transducer while said ultrasonic transducer is longitudinally fixed relative to said first elongate portion in said first mode of operation of said probe for transverse scanning of the tissue; and
translational movement of said moveable member effectuates translational movement of said ultrasonic transducer while said ultrasonic transducer is rotatably fixed relative to said first elongate portion in said second mode of operation for longitudinal scanning of the tissue.

18. A system according to claim 17, further comprising:
a flexible biopsy needle and a flexible cannula which defines a lumen, said needle insertable through said lumen of said cannula.

19. A system according to claim 18, wherein:
said flexible biopsy needle and said cannula are insertable together through said guide channel to a bent configuration in which said needle and said cannula extend through an angle of at least forty degrees from a central longitudinal axis.

20. A system according to claim 18, further comprising:
a biopsy gun coupled to said needle and said cannula and configured to fire said needle and said cannula when said needle and said cannula are disposed in a bent configuration in which said needle and cannula each extend through an angle of at least forty-five degrees from a central longitudinal axis.

21. A system according to claim 16, wherein:
said guide assembly is coupled to said first elongate portion of said probe.

22. A system according to claim 21, wherein:
said guide assembly is longitudinally translatable relative to said probe.

* * * * *